United States Patent [19]
Greenblatt et al.

[11] Patent Number: 6,015,481
[45] Date of Patent: Jan. 18, 2000

[54] ION SELECTIVE SENSORS BASED ON MOLYBDENUM BRONZES

[75] Inventors: Martha Greenblatt, Highland Park; Pavel Shuk, Piscatawy; Kandalam V. Ramanujachary, Deptford, all of N.J.

[73] Assignee: The State University of Rutgers, Piscataway, N.J.

[21] Appl. No.: 09/006,375

[22] Filed: Jan. 13, 1998

Related U.S. Application Data
[60] Provisional application No. 60/035,482, Jan. 13, 1997.

[51] Int. Cl.$^7$ .................................................. G01N 27/26
[52] U.S. Cl. .......................................................... 204/419
[58] Field of Search .............................................. 204/419

[56] References Cited

U.S. PATENT DOCUMENTS
4,111,777  9/1978  Dobson et al. .

OTHER PUBLICATIONS

Tsai, P.P. et al., Crystal Structure of $Li_{0.33}MoO_3$, a Stoichiometric, Triclinic, Lithium Molybdenum Bronze, Journal of Solid State Chemistry 64, 47–56 (1986).

Greenblatt, M., Molybdenum Oxide Bronzes with Quasi–Low–Dimensional Properties, Chem. Rev., 1988, 88, 31–53.

Clearfield, A., Role of Ion Exchange in Solid–State Chemistry, Chem. Rev. 1988, 88, 125–148.

Shuk, P. et al., Molybdenum Oxide Bronzes As pH Sensors, Electrochimica Acta, vol. 41, No. 13, pp. 2055–2058, 1996.

Raistrick, I., Lithium Insertion Reactions in Tungsten and Vanadium Oxide Bronzes, Solid State Ionics 9 & 10 (1983) 425–430.

Raistrick, I., Lithium Insertion Reactions in Oxide Bronzes, Revue de Chimie Minérale, t. 21, 1984, pp. 456–467.

McCarroll, W.H. et al., Preparation of Lithium Molybdenum Oxide Bronzes by a Temperature Gradient Flux Growth Technique, Journal of Solid State Chemistry 54, 282–290 (1984).

Eisenman, G., Glass Electrode for Measuring Sodium Ion, Science, vol. 126, pp. 831–834 (Oct. 25, 1987).

Kress–Rogers, E., Solid–State pH Sensors For Food Aapplications, Trends in Food Science & Technology, Dec. 1991, pp. 320–324.

Randin, J.P., Electrochemical Behavior of Sodium Tungsten Bronze Electrodes in Acidic Media, J. Electrochem. Soc.: Electrochemical Science and Technology, vol. 120, No. 9, Sep. 1973, pp. 1174–1184.

Ramanujachary, K.V. et al, Substitutional Effects on the Electrical Properties of the Purple Bronze $Li_{0.9}Mo_6O_{17}$, Solid State Ionics 22 (1986) 105–115.

Fog, A. et al, Electronic Semiconducting Oxides As pH Sensors, Sensors and Actuators, 5 (1984) 137–146.

(List continued on next page.)

*Primary Examiner*—Terrence R. Till
*Assistant Examiner*—Jennifer McNeil
*Attorney, Agent, or Firm*—Hoffmann & Baron, LLP

[57] ABSTRACT

New solid state pH and sodium ion sensitive metal-oxide-type compositions, sensors and methods are disclosed. Performance thereof was demonstrated at ambient temperature with single crystals of several molybdenum bronzes (i.e. $Na_{0.9}Mo_6O_{17}$, $Li_{0.9}Mo_6O_{17}$, $Li_{0.33}MoO_3$ and $K_{0.3}MoO_3$) The pH sensors with Na-molybdenum-oxide bronzes show near ideal Nernstian behavior in the pH range 3–9. The response is not affected by the direction of the pH change.

28 Claims, 19 Drawing Sheets

OTHER PUBLICATIONS

Dobson, J.V. et al., The Sodium Responsive Tungsten Bronze Electrode An Electrode For Sodium Ion Analysis of DNA Solutions, J. Electroanal. Chem., 220 (1987) 225–234.

Buck, R.P., Crystalline and Pressed–Power, Solid–Membrane Electrodes, Ion–Selective Electrode Methodology, Chapter 9 in Ion Selective Electrodes, ed. A.F. Covington (CRC Press) 1975.

Wakichi, K. et al., Synthesis and Applications of Sodium Tungsten Bronze as an Electrode Material, abstract 121:215712m, Natl. Inst. Mater. Chem. Res., Zairyo Gijutsu, 1994, 12(6), 180–4.

Koksharov, A.G. et al., Electrode Properties of Sodium–Tungsten Bronzes, (abstract) Uch. Zap. Pernisk, Gos. Univ. No. 111, 63–9 (1964).

Wechter, M.A., Use of Metal Tungsten Bronze Electrodes in Chemical Analysis, abstract 121092j, Anal. Chem. 1972, 44(4), 850–3.

Dobon, J.V., et al, Ion Selective Electrodes, Abstract 96:96738e, Mar. 15, 1977.

ION SELECTIVE SENSORS BASED ON MOLYBDENUM BRONZES

CROSS REFERENCE TO RELATED APPLICATION

This application claims priority to U.S. Provisional Application No. 60/035,482 filed Jan. 13, 1997, which is incorporated by reference herein.

The present invention has resulted from investigatory work supported by the State of New Jersey and The Center for Advanced Food Technology (CAFT) which is a New Jersey Commission on Science and Technology Center. The State has certain rights in the invention.

FIELD OF THE INVENTION

Disclosed are solid state metal ion sensors. More particularly, new pH and sodium ion sensors are disclosed which are based on molybdenum bronze oxide compositions. Also disclosed are novel methods and apparatus for using these compositions.

REFERENCES

The following references are cited in this application as bracketed numbers [n]:

[1] G. Eisenman (ed), Glass electrodes for hydrogen and other cations, Marcel Dekker, New York, 1967.

[2] W. Göpel, T. A. Jones, M. Kleitz, I. Lundstrom and T. Seiyama (Eds.), Chemical and Biochemical Sensors, Vol. 2/3, VCH, Weinheim, 1992.

[3] E. Kress-Rogers, Solid state pH sensors for food application, *Trends in Food Science & Technology*, No. 12 (1991) 320–324.

[4] B. Lengyel and E. Blum, The behavior of the glass electrode in connection with its chemical composition, *Trans. Faraday Soc.* 30 (1934) 461–471.

[5] G. Eisenman, D. O. Rudin, and J. V. Vasby, Glass electrode for measuring sodium ion, *Science*, 126 (1957) 831–834.

[6] J. V. Dobson and T. Dickinson, Ion selective electrodes, U.K. Patent No. 1,597,493 (1981).

[7] J. V. Dobson and J. Comer, The sodium responsive tungsten bronze electrode an electrode for sodium ion analysis of DNA solutions, *J. Electroanal. Chem.*, 220 (1987) 225–234.

[8] A. G. Kohsharov and V. F. Ust-Kashkintsev, Electrode properties of sodium-tungsten bronzes, *Uch. Zap. Perm Gos. Univ.*, 111 (1964) 63–69.

[9] A. G. Kohsharov and V. F. Ust-Kashkintsev, Electrode properties of strontium-niobium bronze, *Izv. Vyssh. Ucheb. Zaved. Khim, Khim. Technol.*, 10 (1967) 243–245.

[10] A. G. Kohsharov and V. F. Ust-Kashkintsev, Electrode properties of vanadium oxide bronzes, *Uch. Zap. Perm. Gos. Univ.*, No. 178 (1968) 117–121.

[11] M. A. Wechter, H. R. Shanks, G. Carter, G. M. Ebert, R. Guglielmino and A. F. Voigt, Use of metal tungsten bronze electrodes in chemical analysis, *Anal. Chem.*, 44 (1972) 850–853.

[12] W. Kondo and S. Mizuta, Synthesis and application of sodium tungsten bronze as an electrode material, *Zairyo Gijutsu*, 12 (1994) 180–184.

[13] B. T. Collins, K. V. Ramanujachary, M. Greenblatt, W. H. McCarroll, P. McNally and J. V. Waszczak, Substitutional studies on anisotropic, semiconducting, molybdenum bronze, $Li_{0.33}MoO_3$, *J Solid State Chem.*, 76 (1988) 319-.

[14] R. Brusetti, B. K. Chakraverty, J. Devenyi, J. Dumas, J. Marcus and C. Schlenker, Transport properties of the blue bronze $K_{0.30}MoO_3$, in: Recent Developments in Condensed Matter Physics, Eds. J. T. Devreese et al., Vol. 2, Plenum Press, New York, 1981, 181–190.

[15] A. W. Sleight, T. A. Bither and P. E. Bierstedt, Superconducting oxides of rhenium and molybdenum with tungsten bronze type structure, *Solid State Commun.*, 7 (1969) 299–300.

[16] M. Greenblatt, W. H. McCarroll, R. Neifeld, M. Croft and J. V. Waszczak, Quasi two-dimensional electronic properties of the lithium molybdenum bronze, $Li_{0.9}Mo_6O_{17}$, *Solid State Commun.*, 51 (1984) 671–674.

[17] P. Hagenmuller, Tungsten bronzes, vanadium bronzes and related compounds, in: Comprehensive inorganic chemistry, Vol. 4, Eds. J. C. Bailar et al. (Pergamon Press, New York, 1973) p. 541–605.

[18] M. Greenblatt, Molybdenum oxide bronzes with quasi-low-dimensional properties, *Chem. Rev.*, 88 (1988) 31–53.

[19] P. Shuk, K. V. Ramanujachary and M. Greenblatt, Molybdenum oxide bronzes as pH sensors, *Electrochemica Acta*, 41 (1996) 2055–58.

[20] K. V. Ramanujachary, M. Greenblatt and W. H. McCarroll, Crystal growth of alkali metal molybdenum bronzes by a temperature gradient flux technique, *J. Cryst. Growth.*, 70 (1984) 476–483.

[21] W. H. McCarroll and M. Greenblatt, Preparation of lithium molybdenum oxides bronzes by a temperature gradient flux growth technique, *J. Solid State Chem.*, 54 (1984) 282–290.

[22] J. P. Randin, A. K. Vijh and A. B. Chughtai, Electrochemical behavior of sodium tungsten bronze electrodes in acidic media. *J. Electrochem. Soc.*, 120 (1973) 1174–1184.

[23] A. Fog and R. P. Buck, Electronic semiconducting oxides as pH sensors, *Sensors and Actuators*, 5 (1984) 137–146.

[24] P. P. Tsai, J. A. Potenza, M. Greenblatt and H. J. Schugar, Crystal structure of $Li_{0.33}MoO_3$, a stoichiometric, triclinic, lithium molybdenum bronze, *J. Solid State Chem.*, 64 (1986) 47–56.

[25] I. D. Raistrick, Lithium insertion reactions in tungsten and vanadium oxide bronzes, *Solid State Ionics*, 9/10 (1983) 425–430.

[26] I. D. Raistrick, Lithium insertion reactions in oxide bronzes, *Rev. Chem. Miner.* 21 (1984) 456–467.

[27] M. S. Whittingham and A. J. Jacobson (Eds.), Intercalation chemistry, Academic Press, New York, 1982.

[28] A. Clearfield, Role of ion exchange in solid-state chemistry, *Chem. Rev.*, 88 (1988) 125–148.

[29] A. K. Covington (ed.), Ion-selective electrode methodology, CRC Press, Boca Raton, 1979.

[30] J. Koryta and K. Stulik, Ion-selective electrodes, Cambridge University Press, Cambridge, 1983.

[31] R. A. McCance and E. M. Widdowson, The composition of foods, Elsevier, Amsterdam, 1978.

All of the above cited references are herein incorporated by reference in their entirety to the same extent as if each individual reference was specifically and individually indicated to be incorporated by reference in its entirety.

BACKGROUND OF THE INVENTION

The quick, accurate and reproducible measurement of pH and other ions is important to a number of industries. The ability to accurately measure pH provides important quality parameters in the medical field when it is used for the clinical analysis of blood and other body fluids. Likewise, pH is used as an important quality parameter for the control of milk when it arrives at the dairy, to indicate the freshness of meat, to measure the neutrality of treated industrial wastes and to monitor the acidity of rain.

The ability to measure pH is also an important process control parameter in a number of fermentation process. pH is used to measure the alkalinization of boiler feed water with $NH_3$. pH is also used to monitor the precipitation of heavy metal ions in industrial waste water. In the field of chemistry, pH is used to control the adaptation of redox potentials and to optimize the dissociation of weak electrolytes. pH is also used to monitor the exhaustion of caustic gas scrubber solutions. Also in the field of chemistry, pH is used in the endpoint detection of potentiometric titrations, including in acidimetry, alkalimetry and in the titration of weak acids and bases in organic solvents.

Thus, various types of pH and other ion sensors have been developed to meet the above-referenced needs. In particular, ion sensors have been developed which include for example, chemical and electrochemical sensors. Chemical sensors are measuring devices which convert input variables of a system, such as for example, the concentration of certain species in air, water, solids, solvents, heterogeneous mixtures, or other systems of interest into analytically useful electrical signals.

Electrochemical sensors, however, are the largest and oldest group of sensors. These sensors are divided into three general categories based on what they measure: potentiometric sensors measure voltage; amperometric sensors measure current; and conductimetric sensors measure conductivity. Electrochemical pH sensors include (1) a sensitive electrode (SE) that measures the activity of protons and (2) a reference electrode (RE) whose potential must be constant. The SE and RE are in contact with the solution under investigation. In many cases, the accuracy of potentiometric pH measurements is determined by the reference electrode. Commonly used reference electrodes include silver/silver chloride and mercury/calomel electrodes.

Many problems exist with the use of the above-referenced electrochemical pH sensors. In particular, the reference electrodes are subject to potential drift, can operate only at very narrow temperature ranges, are subject to leakage and chemical reaction between the sample solution and the reference electrolyte and are highly toxic.

Thus, alternatives to electrochemical pH sensors have been developed. An example of such an alternative ion sensor is the sensing electrode. One example of such a sensor is the hydrogen electrode which is formed by a small wire or a small piece of platinized Pt foil over the surface of which pure hydrogen is bubbled. Such electrodes, however, are expensive, difficult to set up and to use. Thus, the hydrogen/platinum electrode nowadays is used only for thermodynarnic investigations or for the accurate determination of the pH values of non-reducible buffer solutions.

The glass pH electrode is another example of a sensing electrode. In recent years, the glass pH electrode has tended to supplant all other types of sensing electrodes for pH measurement [1–2]. For in-line pH sensing, although the glass-electrode is by far the most attractive choice of chemists, it is not suitable for certain applications, such as for example, clinical and food applications. In particular, glass electrodes suffer from the draw back that they are, for example, mechanically fragile, have high impedance and are susceptible to dehydration/alkali errors at low/high pH conditions.

Some of the problems of glass electrodes could be reduced by eliminating the internal reference buffer between the inner glass membrane surface and the Ag/AgCl electrode immersed in this buffer [3]. The problem consists in developing a stable contact that provides a reversible transition from the ionic to the electronic part of the sensor. In view of these problems, emphasis in recent years has shifted to the development of an all-solid-state sensor alternative for the glass electrodes.

Glass electrodes for sodium ion sensing first developed by Lengyed and Blum [4], have been studied systematically for interferences and other limitations by Eisenman et al. [5]. Modern ATI ORION sodium electrodes are glass electrodes with an internal system that eliminates temperature dependent drift. These electrodes are very stable and have relatively fast response times but also have a number of disadvantages: they are affected by fouling of glass, high temperatures, have a limited pH application range (7–11) and cannot be used for certain applications in, for example, the food industry [2].

Several tungsten oxide bronzes having the general formula $A_xM_yWO_3$, where A is Na, K, Rb, Li, Co and Tl and M is K, Li and $NH_4$ in polycrystalline form have been proposed for application as ion selective electrodes by Dobson et al. [6–7]. These investigations, as well as other studies have suggested the use tungsten and other bronzes as pH sensors [8–11] and the application of $Na_xWO_3$ for $Na^+$ sensing [12].

Ternary molybdenum bronzes, for example, have been of interest in recent years due to their interesting physical properties, such as their highly anisotropic transport properties [13–14] and their superconductivity [15–16]. Such compositions have been reviewed by Hagenmuller [17] and in more detail recently by Greenblatt [18]. In contrast to the tungsten bronzes, the molybdenum bronzes (Mo-bronzes) are stoichiometric and more stable. Furthermore, good quality single crystals of the Mo-bronzes used as sensors have clear advantages compared to polycrystalline samples. Preliminary investigations by the inventors have indicated that certain molybdenum bronze single crystals can be used as pH sensors [19]. The inventors have also found that a sodium molybdenum bronze ($Na_{0.9}Mo_6O_{17}$) electrode is sensitive to changes of hydrogen ion concentration, but also shows significant cross sensitivity to other ions, e.g. $Li^+$, $Na^+$, $K^+$.

Accordingly, a need exists for metal oxide pH and sodium ion sensors that are operable over wide pH (3–9) and temperature (20° C.–200° C.) ranges. Furthermore, a need exists for metal oxide pH and sodium ion sensors which are stable, provide highly reproducible readings, have low cross-sensitivity to other ions and are dynamic over a wide range of operating conditions. In particular, a need exists for a pH and sodium ion sensor suitable for use in the food industry that has all of the advantages set forth above and without the disadvantages noted in the prior art. These and other objects which will appear from the following description are obtained with the compositions and devices according to the present invention.

SUMMARY OF THE INVENTION

The present invention is an apparatus for detecting ion concentration in an analyte. This apparatus includes an elongate, generally cylindrical housing that has a proximal end, a distal end, a hollow inner core and an outer surface. A molybdenum oxide bronze ion sensor is supported at one end of the housing for contacting the analyte and detecting an ion concentration in the analyte by establishing an electrical potential corresponding to the ion concentration in the analyte. A processing means is operatively connected to the sensor for converting the electrical potential into a measurement of ion concentration.

Another embodiment of the present invention includes a composition for detecting the concentration of an ion in an analyte. This composition is a molybdenum oxide bronze defined by $A_xMo_yO_z$ (I). In this formula, A is a Group I or a Group II metal as defined in the Periodic Table of Elements and $0<x \leq 1$, $y \leq 100$ and $z \leq 100$. The present compositions can be used as a pH and sodium ion sensors for detecting the pH and sodium ion concentration in an analyte. The present compositions can also be used as pH and sodium ion sensors for use in the food industry, wherein the sensors are molybdenum oxide bronzes defined by formula I above.

Another embodiment of the present invention includes an apparatus for detecting ion concentrations in an analyte. This apparatus includes an elongate probe that has a hollow interior and an outer surface adapted to withstand variations in temperature and pH. The probe has proximal and distal ends. A metal oxide ion sensor is supported at one end of the probe for contacting the analyte and detecting ion concentration therein by generating an electrical potential corresponding to the ion concentration in the analyte. The apparatus further includes a processing means that is operatively connected to the ion sensor for converting the electrical potential into a measurement of ion concentration.

A further embodiment of the present invention is a method for detecting ions in an analyte. This method includes contacting an analyte with an ion detection apparatus. The ion detection apparatus includes a solid state metal oxide ion sensor which is capable of ion exchange with the analyte to form an electrical potential. The method further includes measuring an electrical signal generated by the electrical potential. The electrical signal is then converted into a measurement of the ion concentration of the analyte.

DESCRIPTION OF THE INVENTION

Figure 1:
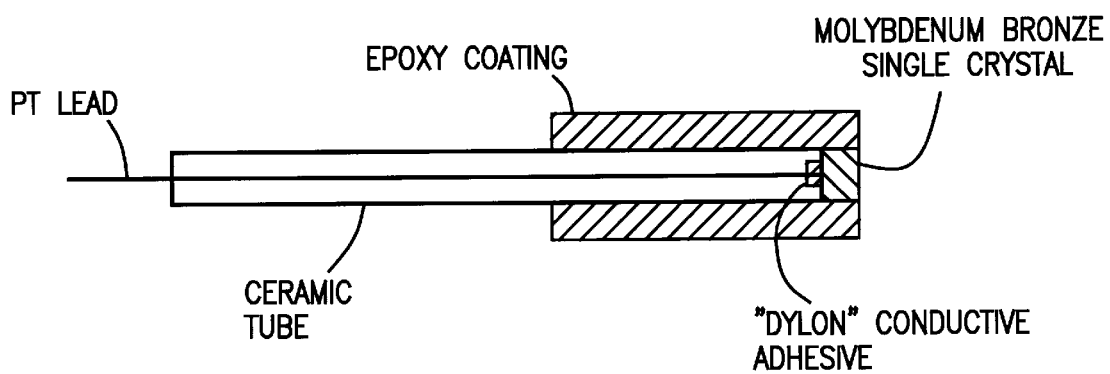
FIG. 1 is a schematic of one embodiment of the ion selective molybdenum oxide bronze electrode of the present invention.
Figure 1A:
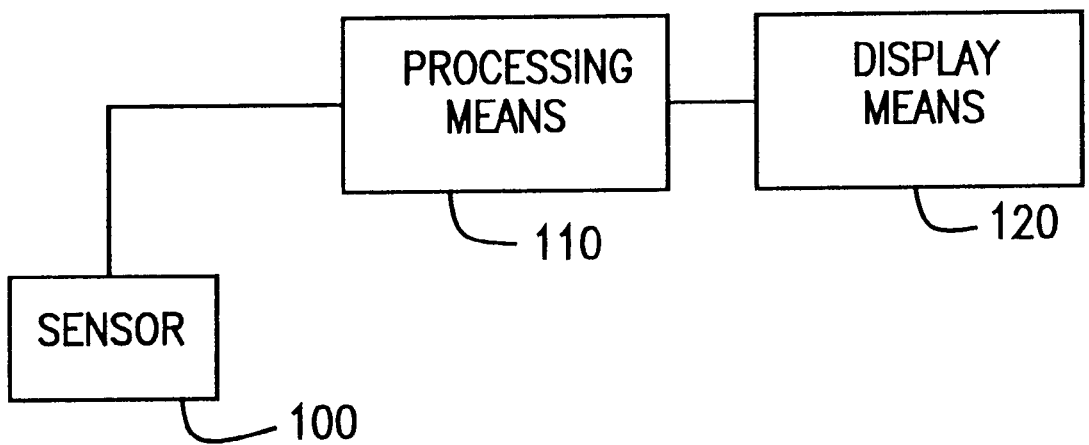
FIG. 1a is a schematic illustration of the present invention including a sensor, a processing means and a display means.

The present invention is an apparatus or device i.e., a cation sensitive electrode, for detecting ion concentrations in an analyte. For purposes of the present invention the terms "apparatus" and "device" are used interchangeably. Such apparati, i.e., ion sensors, are built into an electrode using conventional fabrication techniques. For example, an electrode of the present invention was prepared in a conventional electrode housing by joining a molybdenum oxide bronze ion sensor supported at one end of the housing to a processing means or processor. As depicted in FIG. 1a, sensor 100, which is the molybdenum oxide bronze ion sensor of the present invention (FIG. 1), is operatively connected to processing means 110. The molybdenum oxide bronze sensor establishes an electrical potential corresponding to the ion concentration of the analyte. The processor converts the electrical potential generated by the molybdenum oxide bronze ion sensor into a measurement of ion concentration.

The apparatus of the present invention also includes a display means 120 for displaying the ion concentration of the analyte as determined by the processor 110. Any conventional processor and display means as commonly used in the electrode industry are contemplated by the present invention, such as for example, a computer processing chip and a CRT display screen.

In the present invention, the housing is conventionally designed and fabricated from materials which are typically used to construct pH electrodes. The housing of the present invention, for example, may take the form of an elongate, generally cylindrical probe having proximal and distal ends, a hollow inner core and an outer surface. The housing can be made from a variety of materials conventionally known in the field of electrode construction. Such materials include, for example, ceramics, polymers, metals, composites and combinations thereof. Furthermore, the outer surface of the housing is coated with, for example, a resin, except for a small area of the molybdenum oxide bronze sensor. Other examples of suitable coating materials include, for example, non-conductive polymers, ceramics and composites. Thus, the coating isolates the housing from the analyte and is able to, for example, protect and insulate the housing from the analyte.

A conductor is present within the hollow inner core and extends from the distal end of the housing to the proximal end thereof. The conductor or conducting leads of the present invention include any conventional material that is able to conduct a signal, i.e., an electrical potential generated by the molybdenum oxide bronze compositions of the present invention in response to an ion concentration in the analyte. Such conductors can take any conventionally known form, such as for example a wire or an electrolyte solution. Thus, the conductor may take the form of, for example, a conductive polymer, a metal, an alloy and combinations thereof. In a preferred embodiment, the conductor is a wire made from, for example platinum, gold, copper, silver, aluminum, tungsten, nickel, iron, constantan, nichrome, calorite and combinations thereof. Thus, in the present invention, the conductor is used to operatively connect the molybdenum oxide bronze ion sensor to the processing means.

In one embodiment, a conductive adhesive is used to electrically connect the conductor to the molybdenum oxide bronze sensor. Any conventional conductive adhesive which is capable of operatively connecting the sensor to the conductor may be used with the present invention, such as for example, Dylon adhesives.

The apparatus of the present invention include single crystals and membranes of molybdenum oxide bronze substrates according to formula I:

$$A_x Mo_y O_z \quad (I)$$

wherein A is a Group I or Group II metal as defined in the Periodic Table of Elements and $0<x\leq51$, $y\leq100$ and $x\leq100$. Such substrates can take various forms, including for example, singe crystals, polycrystalline membranes and thin or thick films of about 1,000 Ang. to about 5,000 Ang., respectively. Furthermore, in a preferred embodiment of the present invention, A is Li, Na, K, Rb, Cs and Tl. Similarly, the molybdenum oxide bronze ion sensor can also be represented by $A_{0.33}MoO_3$, where A is Li, Na, K, Rb, Cs and Tl. Moreover the molybdenum oxide bronze ion sensor can also be represented by $A_{0.33}MoO_3$, where A is K, Rb and Tl. The molybdenum oxide bronzes of the present invention include many different crystalline structures, such as for example, $Na_{0.9}Mo_6O_{17}$, $Li_{0.9}Mo_6O_{17}$, $Li_{0.33}MoO_3$ and $K_{0.3}MoO_3$. Furthermore, the sensitive element of the molybdenum oxide bronze ion sensor includes the following formula:

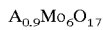

$$A_{0.9}Mo_6O_{17}$$

where A is, for example, Li, Na, K, (Na/Li), (Na/K), (Na/Rb) and (NalCs). Similarly, the molybdenum oxide bronze ion sensor can also be represented by $A_{0.33}MoO_3$, where A is Li, Na, K, Rb, Cs and Tl. Moreover, the molybdenum oxide bronze ion sensor can also be represented by $A_{0.3}MoO_3$ where A is K, Rb and Tl. The molybdenum oxide bronzes of the present invention can be prepared by conventionally known methods in the art, such as for example, by temperature gradient flux techniques as described elsewhere [20–21].

The molybdenum oxide bronze substrate of the present invention is supported on one end of the housing. Any conventionally known technique can be used to attach the substrate to, for example, the distal end of the housing so long as the resulting configuration is functional. The membrane or crystal substrate, for example can be embedded in, e.g., the distal end of the housing so that one surface thereof is available to be connected to the conducting lead and one surface is contiguous with the outer surface of the housing and is available to be immersed in the analyte for detecting ion concentrations.

The devices of the present invention are especially suited for measuring cation concentrations, although other types of ion species can also be measured using the present sensors. In a preferred embodiment, however, the ion sensor of the present invention is used to measure hydrogen ion concentrations (pH) and/or sodium and potassium ion concentrations. Furthermore, the devices of the present invention can be used to measure ion concentrations in many commercial, scientific and industrial settings. The present devices, however, are especially suited for measuring to ion concentrations in the clinical setting and in the food industry. In particular, the present devices are well adapted for measuring ion concentrations in comestibles, such as for example, in water, milk, soups, gravies, soda, alcohol, as well as in meats, poultry and fish.

The cation sensitive electrodes of the present invention were fabricated by attaching conducting leads, such as a platinum wire, as set forth above, to the molybdenum oxide bronze single crystals or membranes with a "Dylon" conductive adhesive and coating the entire assembly with a resin. Although Dylon conductive adhesives are preferred, any conventional conductive adhesive consistent with the operation of a pH or sodium ion sensing electrode can be used with the present invention.

As set forth above, the outer surface of the housing is coated to isolate the housing from the analyte with, for example, a chemically resistant material. Any conventional coating material as used in the electrode field may be used to coat the outer surface of the housing, such as for example, epoxy resins. A small area of the crystal or membrane surface, however, must be left exposed, i.e. not coated, so that it can be used for sensing (FIG. 1).

The pH sensing characteristics of the membranes of the present were evaluated by measuring their e.m.f. against a standard Ag/AgCl reference electrode with a Fisher Accumet 15 high impedance pH meter. The pH response of the electrodes was monitored in commercially available buffer solutions, hydrochloric acid, different bases as well as in some titration systems.

The sodium ion sensing characteristics of the crystal membranes were evaluated by measuring their e.m.f. against a standard Ag/AgCl reference electrode. Aqueous solutions of sodium nitrate or chloride of varying pH were prepared by the addition of hydrochloric acid or sodium hydroxide solutions. The K+concentration was varied by the addition of potassium nitrate solutions. A fresh solution was used for each sodium ion concentration measurement. The electrode was rinsed between each measurement with sodium electrode rinse solution (0.01 M $NaNO_3$) to maintain an $Na^+$-sensing film on the surface of the molybdenum bronze crystal.

It is assumed that pH and other ion sensing properties of molybdenum oxide bronze electrodes depend on cation-exchange reactions similar to those proposed for the tungsten bronze electrodes [22–23], therefore the structure of molybdenum oxide bronzes has to be considered. The $A_xWO_3$ phases are wide range non-stoichiometric compounds ($0<x\leq1$), all formed with perovskite-like structures. The molybdenum oxide bronzes of the present invention are stoichiometric or nearly so [18], however, there are three different classes of the ternary phases based on stoichiometry and structure.

The ion sensors of the present invention include several classes of molybdenum bronze oxide substrates, including for example, the blue bronzes, the purple bronzes, the red bronzes and combinations thereof. As set forth above, the first class of molybdenum oxide bronzes are known as the blue bronzes ($A_{0.3}MoO_3$, where A=K, Tl or Rb and $Mo_{avg}$=+5.7). The blue bronzes are quasi-one-dimensional and have a metal-semiconductor transitional 180K which is due to a CDW. The second class of molybdenum oxide bronzes are known as the purple bronzes ($A_{0.9}Mo_6O_{17}$, where A=Na, K or Tl [A=1.0] and $Mo_{avg}$=+5.50. The purple bronzes are quasi-two-dimensional metals having a metal-metal transition at a temperature (T) which is dependent on the A cation. The purple bronzes demonstrate a CDW instability where A is Na, K and most likely Tl as well. Another member of the purple bronze family is $Li_{0.9}Mo_6O_{17}$. This purple bronze composition is a quasi-one-dimensional metal which has an upturn in $\rho$ at 24 K and is a superconductor at 1.9 K. The red bronzes are the third class of molybdenum oxide bronzes. An example of such a composition is $A_{0.33}MoO_3$, where A+K, Tl, Rb or Cs and $Mo_{avg}$=+5.67. This composition is a semiconductor and the $\rho(298)=10^4-10^5$ $\Omega$cm. Another example of a red bronze composition is $Li_{0.33}MoO_3$. This composition has a violet color, is structurally unique and its $\rho(298)=0.2$ $\Omega$cm.

$Na_{0.9}Mo_6O_{17}(K_{0.9}Mo_6O_{17})$

More particularly, the structure of the hexagonal, purple bronze, $K_{0.9}Mo_6O_{17}$ can be described in terms of slabs of Mo—O corner sharing polyhedra. The idealized structure of $K_{0.9}Mo_6O_{17}$ viewed in FIG. 2 along the a axis shows the ininite layers of comer-sharing molybdenum-oxygen polyhedra stacked along the c axis and held together by $K^+$ ions in a $KO_{12}$ icosahedral environment of oxygens.

$K_{0.3}MoO_3$

Figure 3:
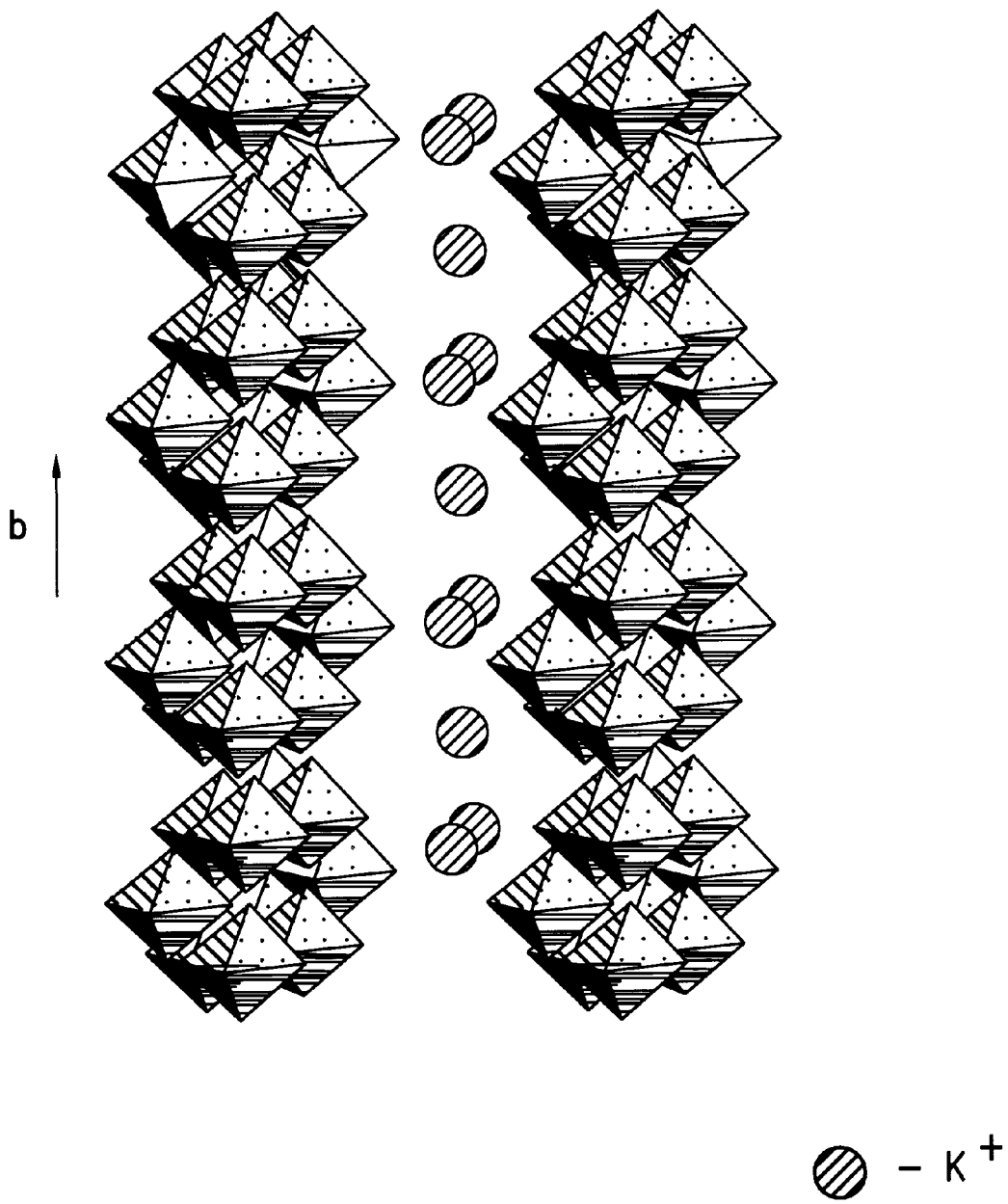
FIG. 3 is a crystal structure of $K_{0.3}MoO_3$ according to the present invention.

The structure of $K_{0.3}MoO_3$ is built of $ReO_3$-type infinite sheets of distorted $MoO_6$ octahedra held together by $K^+$ cations (FIG. 3). The unit of structure is ten edge- and corner-sharing $MoO_6$ octahedra, which corner share to form the infinite sheets along the [010] and [012] directions.

$Li_{0.33}MoO_3$, $Li_{0.9}Mo_6O_{17}$

Figure 4:
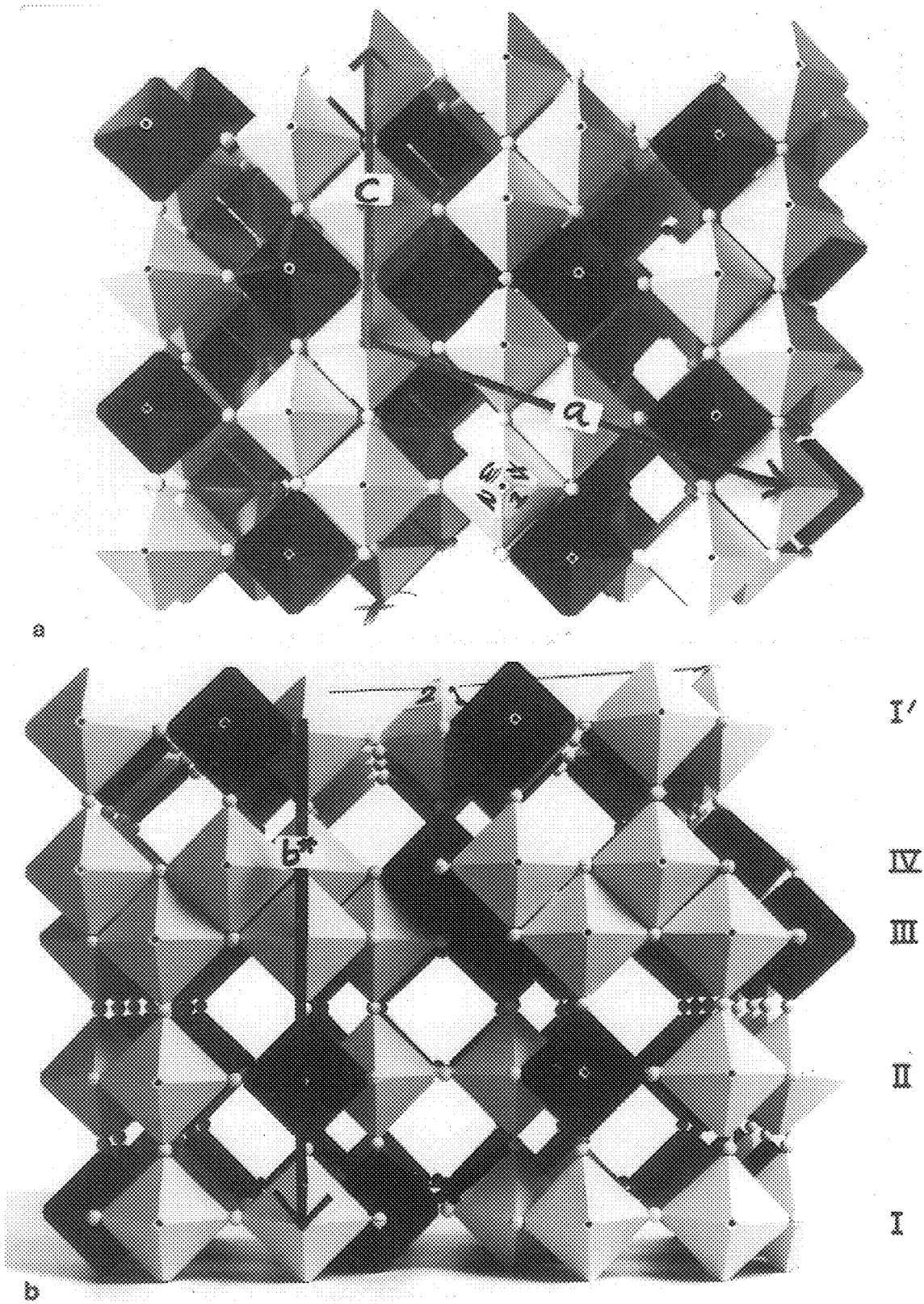
FIG. 4 is a crystal structure of $Li_{0.33}MoO_3$ according to the present invention.
Figure 5:
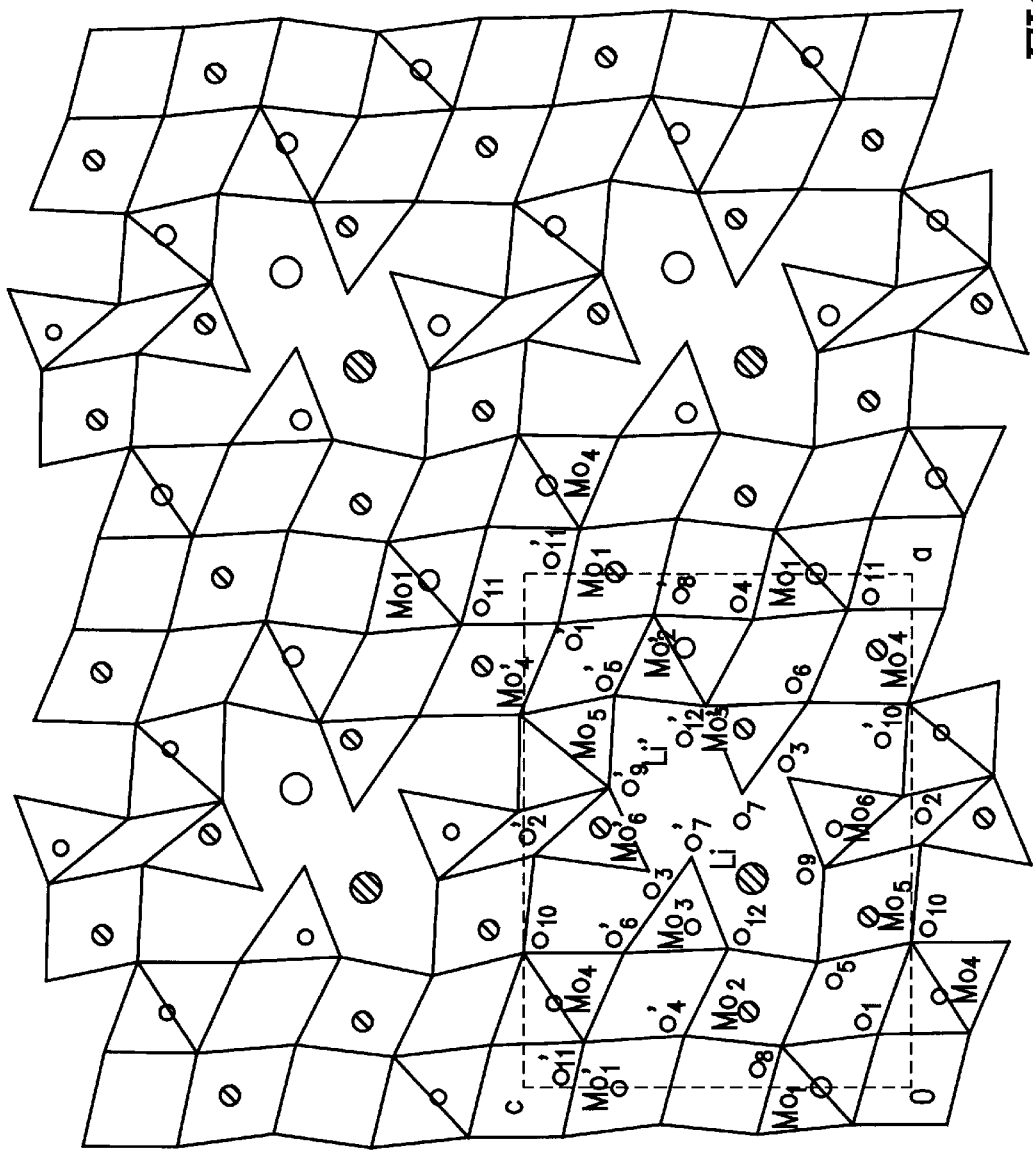
FIG. 5 is a crystal structure of $Li_{0.9}Mo_6O_{17}$ projected in the ac plane. Open and hatched circles indicate atomic positions at y=¼ and ¾, respectively [18].

The crystal structures of the Li—Mo—O bronzes are unique. Because of the small size of the $Li^+$ ion, three dimensional (3D) interconnected network structures form instead of the layer-like structures favored by the $A_{0.3}MoO_3$ (A=K, Rb, Tl) blue and $A_{0.9}Mo_6O_{17}$ (A=Na, K, Tl) purple bronzes discussed above. The structure of $Li_{0.33}MoO_3$ can be viewed as derived from an $ReO_3$-type shear structure of $V_2O_5$-like layers in the ac plane with every fourth octahedron in the edge-shared zigzag chains being a $LiO_6$ octahedron [24]. These layers stack long the b* direction by edge and comer sharing (FIG. 4). The structure of $Li_{0.9}Mo_6O_{17}$ is similar to that of the other $A_{0.9}Mo_6O_{17}$ phase (FIG. 2), except that in the corresponding "c" direction of the Li-phase, $MoO_6$, and $MoO_4$ polyhedra share corners to create a 3D network structure (FIG. 5). The $Li^+$ ions are located in the large cavities at similar locations as the A cations in the layered structures.

The structure of the Mo-bronzes is relatively open for cation-insertion or ion-exchange reactions, similar to other oxide bronzes, i.e., tungsten or vanadium oxide bronzes [25–26]. Due to the complex geometry of the crystal lattice of the molybdenum oxide bronzes, a distribution of ion-exchange site enthalpies and consequently the complex ion-exchange processes would be expected. Furthermore, the structure of the molybdenum oxide bronze electrode subsurface, which determines the sensing properties will be significantly different from that of the bulk structure.

Ion-exchange properties of bronzes

Figure 6:
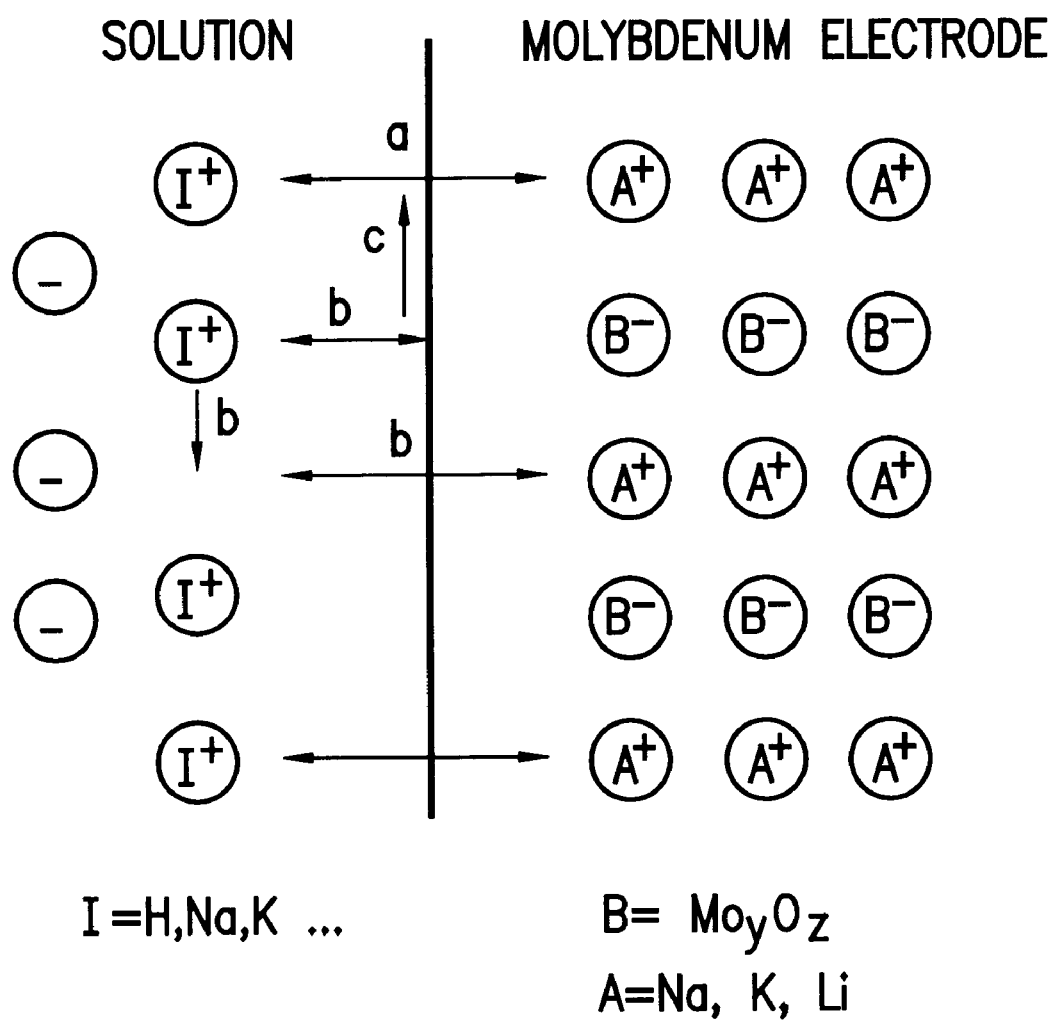
FIG. 6 is a schematic view of ion exchange at an interface of the molybdenum ion-selective electrode of the present invention.

The ideal ion-sensitive sensor should be structurally stable over a wide temperature range and provide uniform ion-exchange capacity in the measured ion-activity range [23]. In the case of layered oxides such as $MoO_3$, the hydrated alkali metal and hydrogen species can be replaced and interchanged by ion exchange from aqueous electrolyte solutions [27]. Similarly, when the molybdenum oxide bronze electrode contacts a solution, surface hydrolysis may occur and a proton or other ion exchange process establishes an interfacial potential between the solution and the bronze electrode surface (FIG. 6). The measured potential difference depends on the pH, or the i concentration of other ions in solution when the solution/electrode interface is reversible with respect to ion, i.e. proton, exchange and the electrode/substrate (connector) is electronically reversible. At the ion-sensitive electrode surface, ions may enter in various steps. An ion from solution can cross the interface and exchange (FIG. 6, vector a). If the ion approaches the electrode surface at an inactive site, back diffusion occurs on the surface of the sensor to an active site (FIG. 6c). The charge transfer is the next step in the electrode reaction when the primary ion crosses the interface to participate in the ion-exchange process.

The rate-determining step in the ion-exchange is the counter diffusion of ions within the solid, provided the concentration of in-going ions at the surface is high enough and stirring does not allow undue concentrations of the out-going ions to accumulate at the surface of the exchange electrode. Small particle size and larger interdiffusion coefficients favor rapid ion exchange [28]. Of course, the mechanism depicted in FIG. 6 is overly simplified. The hydration of the ions, prior to adsorption of the ion complex (e.g. $[H(H_2O)_n]^+$) on surface oxygens and/or formation of hydroxyl groups on the surface and surface diffusion of the exchanging species are expected to take place.

$Na_xWO_3$

The composition of the surface layer of the electrode during the electrochemical reaction is believed to change according to the following insertion redox process [22–23]:

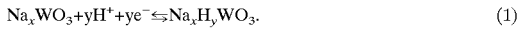

$$Na_xWO_3+yH^++ye^-\leftrightarrows Na_xH_yWO_3. \qquad (1)$$

In contrast, reaction (2)

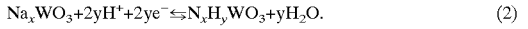

$$Na_xWO_3+2yH^++2ye^-\leftrightarrows N_xH_yWO_3+yH_2O. \qquad (2)$$

is less likely to be the equilibrium process involved in pH sensing, because it requires the breaking of a tungsten-oxygen bond, which is expected to be energetically less probable than the diffusion of a hydrogen ion and an electron transfer required to adjust the oxidation state of tungsten. Then, if $N_xH_yWO_3$ is regarded as a solid solution of hydrogen atoms in the oxide network, the electrode potential for reaction (1) is be given by:

$$\Delta\phi=(1/F)(\mu_H^++\mu^Se^--\mu^S_H)=\text{const}+RT/F\ln(a_{H^+})-RT/F\ln(a^S_H), \qquad (3)$$

where $\mu^S_H$ and $a^S_H$ are the chemical potential and the activity of hydrogen, respectively, in the solid solution phase (subsurface layer of the oxide bronze).

Thus, the electrode responds to hydrogen ions in the solution ($a_{H^+}$), as well as to hydrogen activity ($a_H$) in the solid-solution phase. The insertion process (Eq. 1) is probably limited to the subsurface region of the bronze electrode.

$A_xMo_yO_z$

The exact mechanism by which the molybdenum oxide bronze electrodes of the present invention respond to changing pH conditions is not clear at present. Because the ion-exchange-type pH sensors involve bulk and/or surface ion conductivity, two possible mechanisms can be proposed to explain such Mo-bronze pH sensing activity and are set forth below. These mechanisms are purely explanatory in nature and are not intended to limit the scope of the present invention in any way. These mechanisms are expressed as follows:

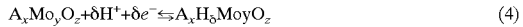 (4)

or

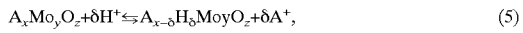 (5)

where proton insertion or exchange is taking place similar to that suggested for the tungsten bronze pH sensors by Fog and Buck [23]. In the case of molybdenum bronzes, oxygen deficiency and the formation of an oxygen deficient phase ($A_xMo_yO_{z-\delta}$) is also unlikely. Thus, similar to the tungsten bronze electrode, if $A_xH_\delta Mo_yO_z$ is considered as a solid solution of hydrogen atoms in the oxide, the electrode potential for reaction (4) or (5) may be given by:

$$\Delta\phi = (1/F)(\mu_H^+ + \mu^S e^- - \mu^S_H) = \text{const} + RT/F \ln(a_H^+) - RT/F \ln(a^S_H). \quad (6)$$

or $$\Delta\phi = (1/F)(\mu_H^+ + \mu^S e^- - \mu^S_H - \mu_A^+) = \text{const} + RT/F \ln(a_H^+) - RT/F \ln(a^S_H) - RT/F \ln(a_A^+), \quad (7)$$

respectively. The electrical potential ($\Delta\phi$) depends on the hydrogen ion ($a_{H^+}$) or A-ion ($a_A^+$) activity in solutions, as well as on hydrogen activity in the solid phase. Calculations based on idealized model cation-exchange systems are difficult to apply to molybdenum oxide bronze systems for the same reasons as those for real glass systems [1]. It is the cation-charged surface film (or subsurface layer) of the molybdenum oxide bronze that determines the electrode properties rather than the bulk composition of the molybdenum bronze single crystal. The composition of this film (or layer) is undoubtedly substantially different from that in the interior of the crystal, and is, in general, in real systems unknown and/or can not be controlled. Regarding the cation-exchange by ions other than protons in molybdenum oxide bronze electrodes, the potential difference can be expressed by the Nikolskij-Eisenman equation:

$$E = \text{const} + RT/F \ln(a_H^+ + \Sigma K_{H^+, i} \cdot a_i^{1/z}) + X, \quad (8)$$

where X depends on the proton (or other cation) activity in the subsurface layer of the molybdenum oxide bronzes and $K_{H+,i}$ is the selectivity constant for the exchange of $H^+$ for other ions, i; $a_i^{1/z}$ is the activity of another ion with charge z in solution. The lower value of the selectivity constant $K_{H+,i}$ and the activity of the i-ion, the more selective for hydrogen (or other) ion the ion membrane molybdenum bronze electrode will be.

The plot of measured e.m.f. (E) vs. pH (or $pA = -\log a_A^+$, where A=Li, Na, K) should yield a straight line with a slope ~59 mV/pH at 25° C. when the activity of protons (or other ions) in the subsurface layer of the molybdenum bronze is assumed constant at the conditions of the measurement and the interference of other ions is not significant.

pH Sensing

Figure 7:
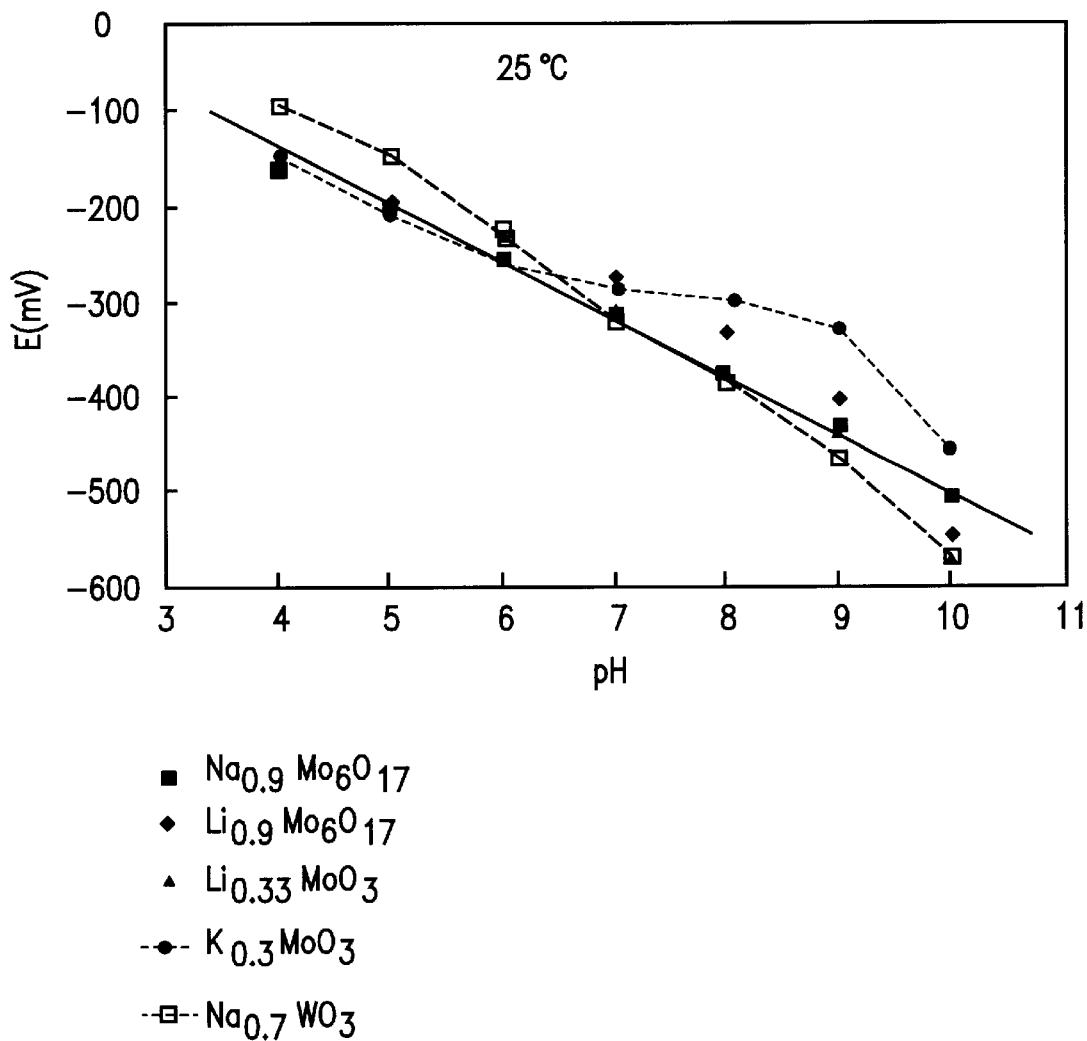
FIG. 7 is a graph showing the pH response of various single crystals of molybdenum oxide bronzes as sensors according to the present invention.
Figure 8:
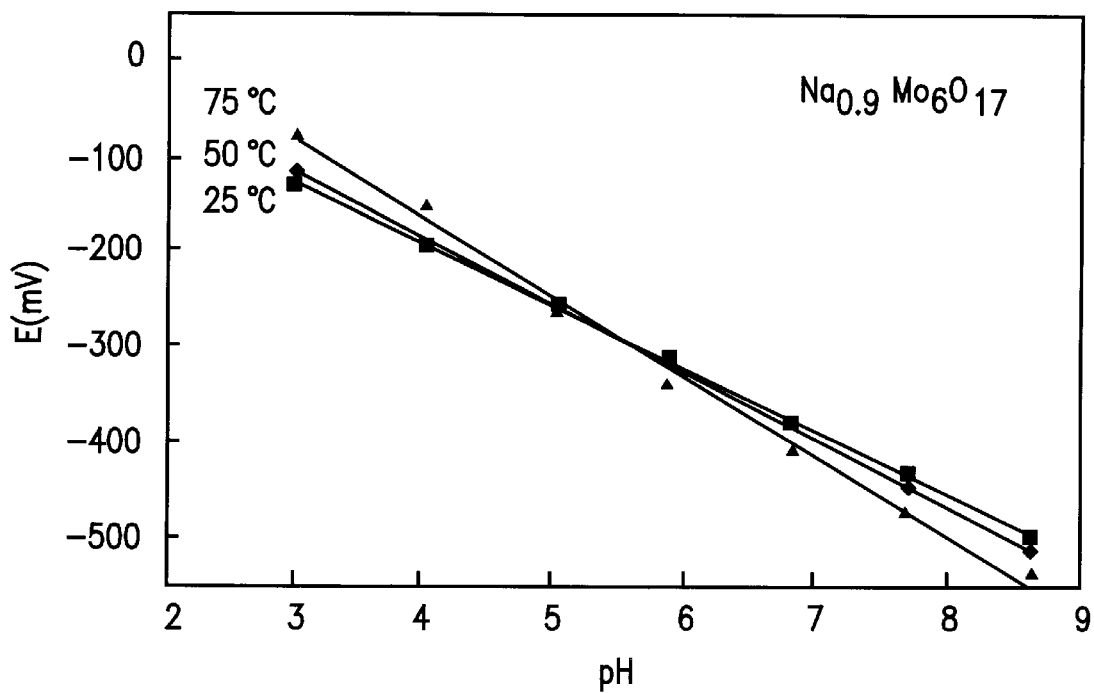
FIG. 8 is a graph showing the temperature dependent pH response of a $Na_{0.9}Mo_6O_{17}$ sensor according to the present invention.

As shown in FIG. 7, pH sensors of the present invention with different molybdenum oxide bronze single crystals as the sensitive electrode show linear behavior in the pH range 3–9 at room temperature with a slope of about −59–60 mV/pH. Thus, the hydrogen activity in the molybdenum oxide bronzes of the present invention at the conditions of the measurement is nearly constant. The response was unaffected by the direction of the pH change. In contrast, the pH sensor of a prior art Na-tungsten bronze sensitive electrode shows deviation from linearity, as well as Nernstian behavior with a slope −76.3 mV/pH at 25° C. (FIG. 7). It has also been established reproducibly that strong acids or strong bases suppress the sensitivity of the Mo-bronze pH sensors of the present invention. This finding supports a proton exchange mechanism of pH sensing in single crystals of molybdenum oxide bronzes. When the temperature of the analyte solution is increased, molybdenum oxide bronze pH electrodes also show Nernstian response with −64 mV/pH and −69 mV/pH slopes at 50° C. and 75° C., respectively (FIG. 8).

Figure 9:
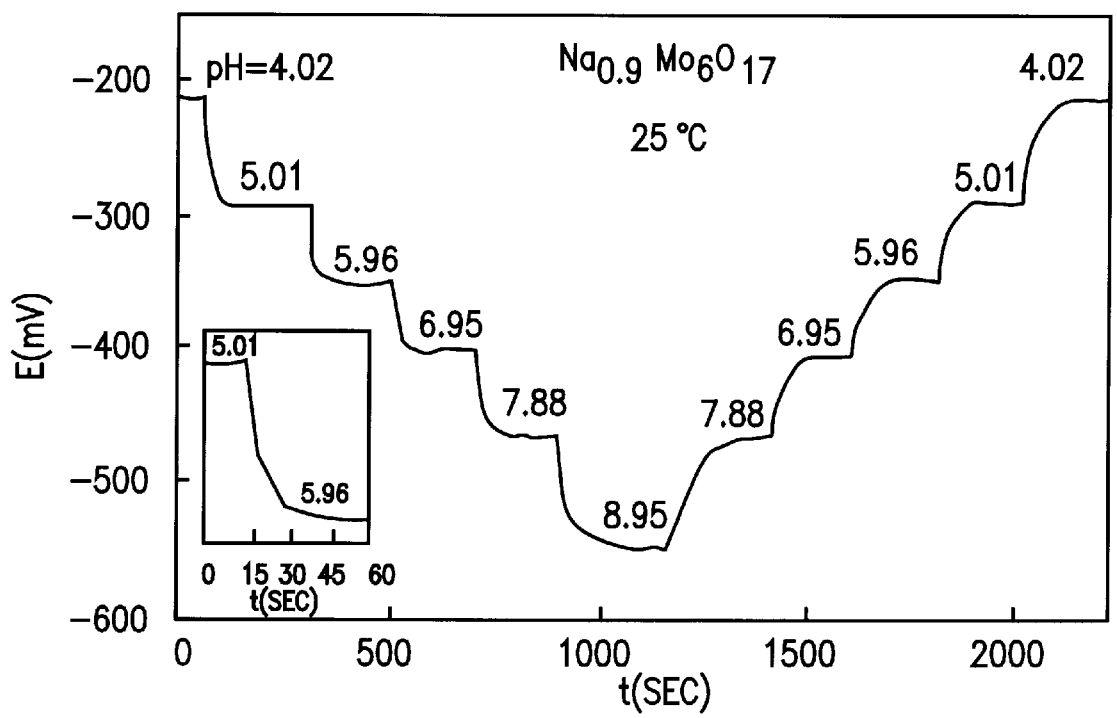
FIG. 9 is a graph showing the dynamic pH response of a $Na_{0.9}Mo_6O_{17}$ single crystal sensor according to the present invention.

The Na- or Li-molybdenum bronze sensors of the present invention are extremely sensitive to changes of pH of the analyte. FIG. 9 represents typical dynamic behavior of the molybdenum bronze pH sensors of the present invention with a $Na_{0.9}Mo_6O_{17}$ composition as the sensitive electrode. The response time of the $Na_{0.9}Mo_6O_{17}$ sensor to pH changes in a wide range of pH is less than five (5) seconds for 90% response, except at high proton concentrations (low pH). In the latter case, proton exchange or insertion is probably the limiting factor. Similar response behavior is observed with other molybdenum bronze pH sensors. Tests with prior art tungsten bronze ($Na_xWO_3$) sensors showed unstable responses in the 4–9 pH range.

In another embodiment of the present invention, a composition is provided for detecting ion concentrations in an analyte. This composition is a molybdenum oxide bronze defined by formula I above: $A_xMo_yO_z$ wherein A is wherein A is a Group I or Group II metal as defined in the Periodic Table of Elements and $0<x\leq 1$, $y<100$ and $x\leq 100$. As set forth above, this composition includes blue, purple and red molybdenum oxide bronzes, as well as combinations thereof.

In one embodiment of the present invention, the molybdenum oxide bronze composition includes, for example, $K_{0.3}MoO_3$, $Tl_{0.3}MoO_3$, $Rb_{0.3}MoO_3$, $Li_{0.33}MoO_3$, $Na_{0.9}Mo_6O_{17}$, $K_{0.9}Mo_6O_{17}$, $Tl_{0.9}Mo_6O_{17}$, $Li_{0.9}Mo_6O_{17}$, $K_{0.33}MoO_3$, $Tl_{0.33}MoO_3$, $Rb_{0.33}MoO_3$, $Cs_{0.33}MoO_3$, $(Na_{0.5}Li_{0.5})_{0.9}Mo_6O_{17}$ and combinations thereof. As set forth previously, the molybdenum oxide bronze compositions of the present invention can take any conventional form, such as for example, crystals, polycrystalline membranes and thick and thin films which are suitable for measuring the ion concentration of an analyte.

Many different crystalline forms of the molybdenum oxide bronzes of the present invention can be used as ion sensors. Such crystalline forms include, for example, the structures depicted in FIGS. 2, 3, and 4 for $K_{0.9}Mo_6O_{17}$, $K_{0.3}MoO_3$ and $Li_{0.33}MoO_3$, respectively.

Thus, as set forth previously, the molybdenum oxide bronze compositions of the present invention can be used in pH, sodium and potassium ion sensors in any conventional form including, for example as single crystals and as membranes. Thus, such compositions can be integrated into ion sensors which are useful in many industrial, commercial and scientific applications, including for example, in the food, automobile, health-related, industrial waste and rain water management industries.

Another embodiment of the present invention includes an apparatus for detecting ion concentrations in an analyte. This apparatus includes an elongate probe having a hollow interior and an outer surface adapted to withstand variations in temperature and pH. The present probes are designed to function in temperatures which range from, for example, about 20° C. to about 200° C. Furthermore, these probes are designed to withstand extremes in pH from about 3 to about 9 pH units. These probes have proximal and distal ends. Any conventional probe construction compatible with the present metal oxide sensors may be used in the manufacture of the present apparatus.

A metal oxide ion sensor is supported at one end of the probe so that at least a part of the sensor is freely accessible to the analyte. The metal oxide sensor must be located on the probe in such a manner that it is able to contact the analyte and detect the ion concentration therein by generating an electrical potential in response to the ion concentration of the analyte. The metal oxide ion sensor is a molybdenum oxide bronze as described in detail above.

A conventional processing means, such as for example, a silicon computer processing chip, is operatively connected to the metal oxide sensor for converting the electrical potential into a measurement of ion concentration.

A conductor, as described previously, is disposed within the hollow interior of the probe and is operatively connected to the metal oxide ion sensor at, for example, the distal end of the probe. The connection between the metal oxide sensor and the conductor is made using a conductive adhesive, such as Dylon as described above. As set forth above, a processing means is operatively connected to the conducting means for processing ion concentration signals generated by the sensor. A display means, such as a CRT or other such device, is operatively connected to the processing means for displaying ion concentration information. The connections between the conductor, the processing means and the display means are those which are conventionally known and used within the art. Thus, the apparatus of the present invention set forth above is able to measure ion concentration of, for example hydrogen ions (pH) and/or potassium and sodium ions over great variations of temperature, i.e., between about 20° C. and about 200° C., and pH , i.e., between about 3 and about 9.

In a further embodiment of the present invention, a method is provided for detecting ions in an analyte. This method includes contacting an analyte with an ion detection apparatus substantially as described above. This ion detection apparatus is a solid state metal oxide ion sensor which is capable of ion exchange with the analyte to form an electrical potential. The method further includes measuring an electrical signal generated by the electrical potential. The electrical signal is then converted into a measurement of ion concentration by, for example, a computer processor. The signal is then displayed on, for example, a CRT device. The processor and display device, as set forth previously, can be any conventionally known processor and display typically used in the electrode industry.

In the method of the present invention, the metal oxide sensor corresponds to formula (I) set forth previously: $A_xMo_yO_z$ (I), wherein A is a group I or a group II metal as defined in the Periodic Table of Elements and $0<x\leq1$, $y<100$ and $z<100$.

The following examples are set forth to illustrate the molybdenum oxide bronze sensors of the present invention. These examples are provided for purposes of illustration only and are not intended to be limiting in any sense.

EXAMPLE 1

Titration Curves

Figure 10:
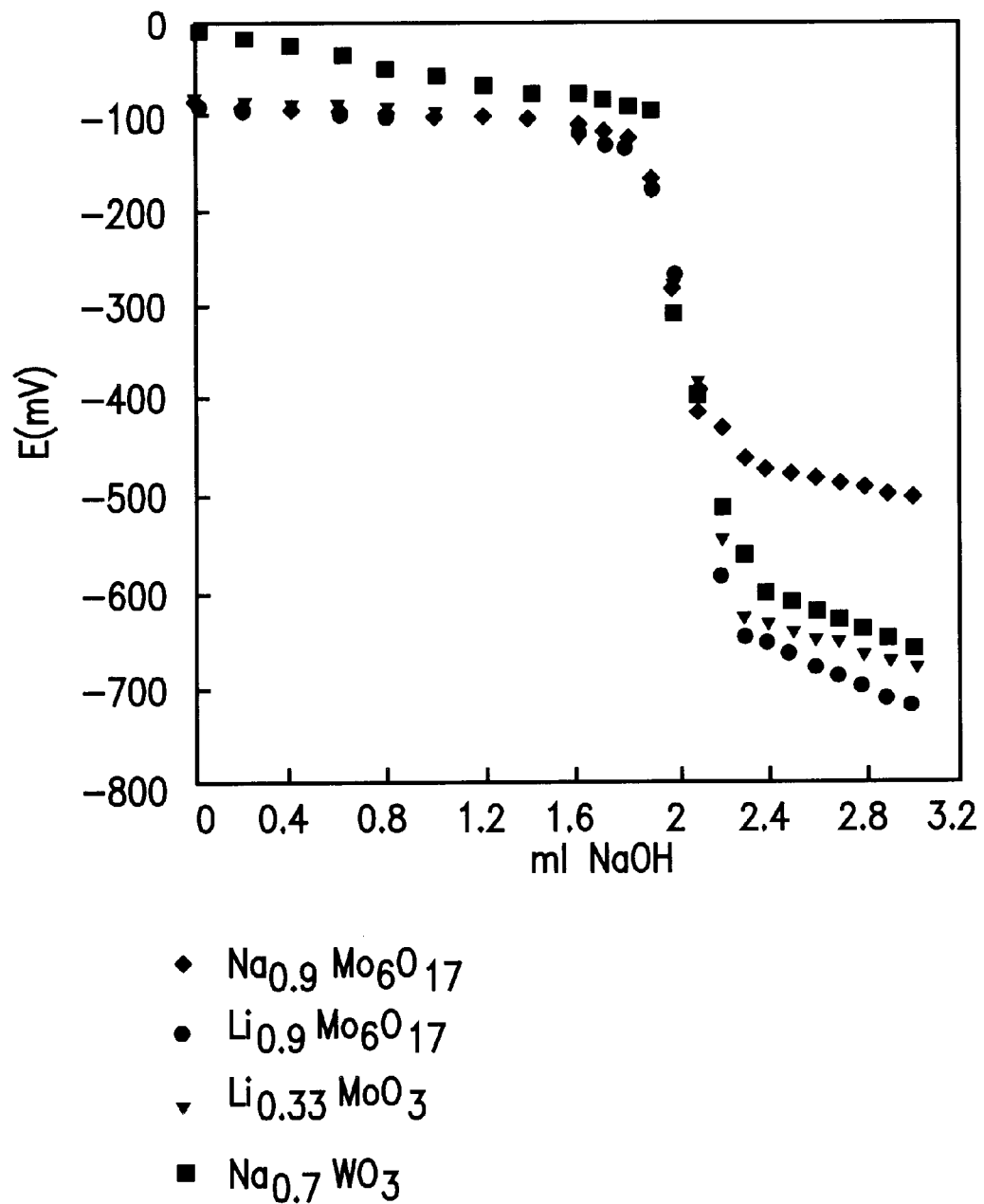
FIG. 10 is a graph showing the titration of 0.0017 MHCl with 0.1 MNaOH with various molybdenum oxide bronze pH sensors according to the present invention.

A number of titrations were performed in aqueous media. In the titrations, a pH sensor of the present invention consisted of a molybdenum oxide bronze single crystal or a prior art tungsten crystal as the sensing electrodes and saturated Ag/AgCl served as a reference electrode. Some of these titrations were also performed with glass electrodes. The titration curves with the bronze sensing electrodes of the present invention closely resembled those of the glass electrode. Although the sensitivity and response of the molybdenum oxide bronze electrodes were better, the end point with the glass electrode was slightly different (FIG. 10).

EXAMPLE 2

Cross-Sensitivity Tests

No ion-selective electrode is entirely selective towards the ion specified. The presence of other ions can seriously impair sensing performance. Such interferences can take several forms, depending on the type of electrode material [29–20].

Figure 11:
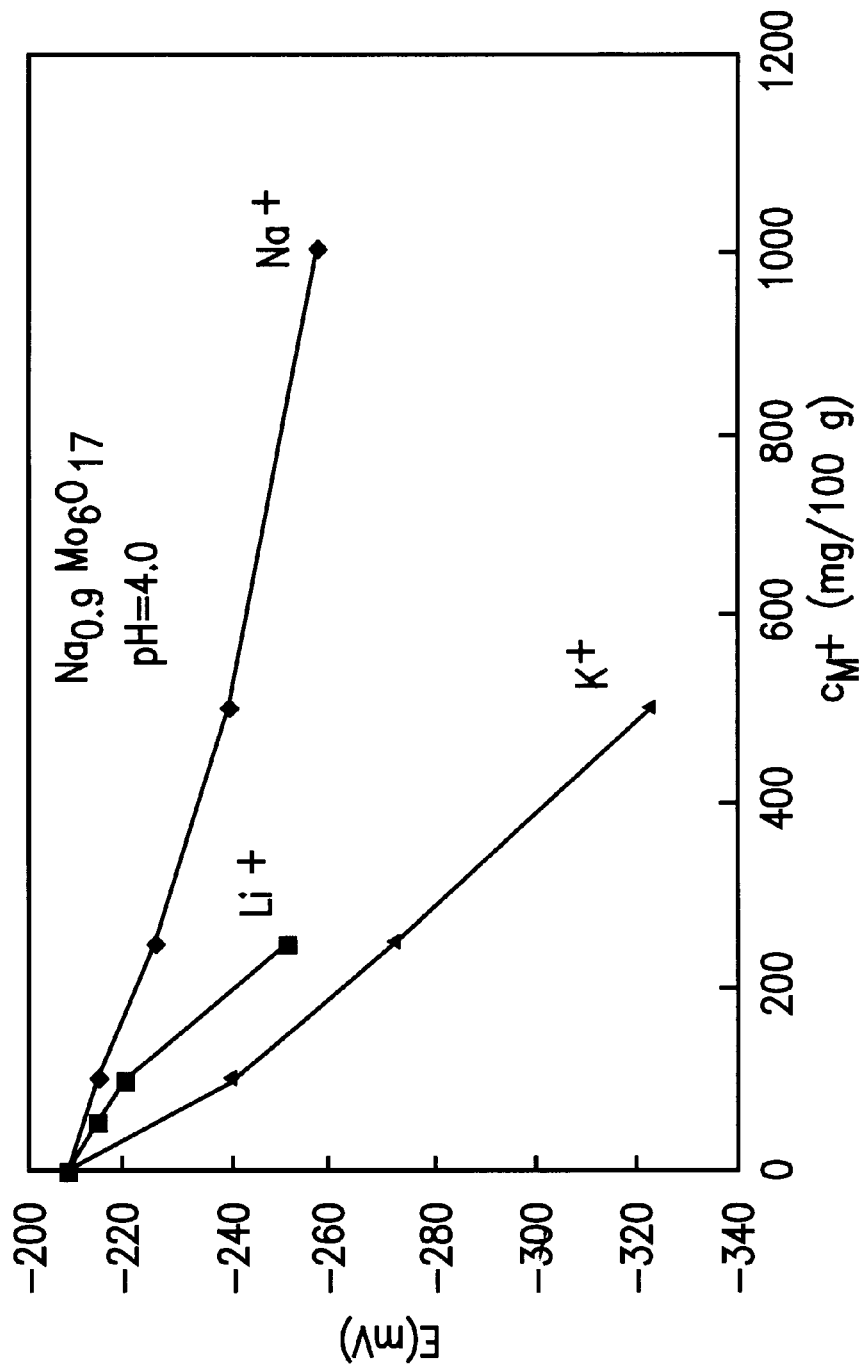
FIG. 11 is a graph showing the cross-sensitivity tests of $Na_{0.9}Mo_6O_{17}$ pH electrodes to $Li^+$, $Na^+$ and $K^+$ ions.

Cross-sensitivity tests of pH sensors with single crystals of $Na_{0.9}Mo_6O_7$ show significant selectivity error in solutions containing $K^+$, $Na^+$, $Li^+$ (FIG. 11). Furthermore, these electrodes were reduced and/or complexed on the surface by iodide ions. Potential increases were observed of some 10 mV with $Na_{0.9}Mo_6O_{17}$ as pH sensor in buffer solutions by changing $K^+$- or $Na^+$- concentration in the range 0–1000 mg/100 g and 0–500 mg/100 g, which are typical concentration ranges of these ions present in different liquid foods [31]. The Li-molybdenum bronze electrode $Li_{0.33}MoO_3$, of the present invention, however, appears to be highly selective to $H^+$ ions consistent with its 3D structure, the smaller size of the interstitial cavities and the more tightly bound $Li^+$ ions.

pNa sensors

Figure 12:
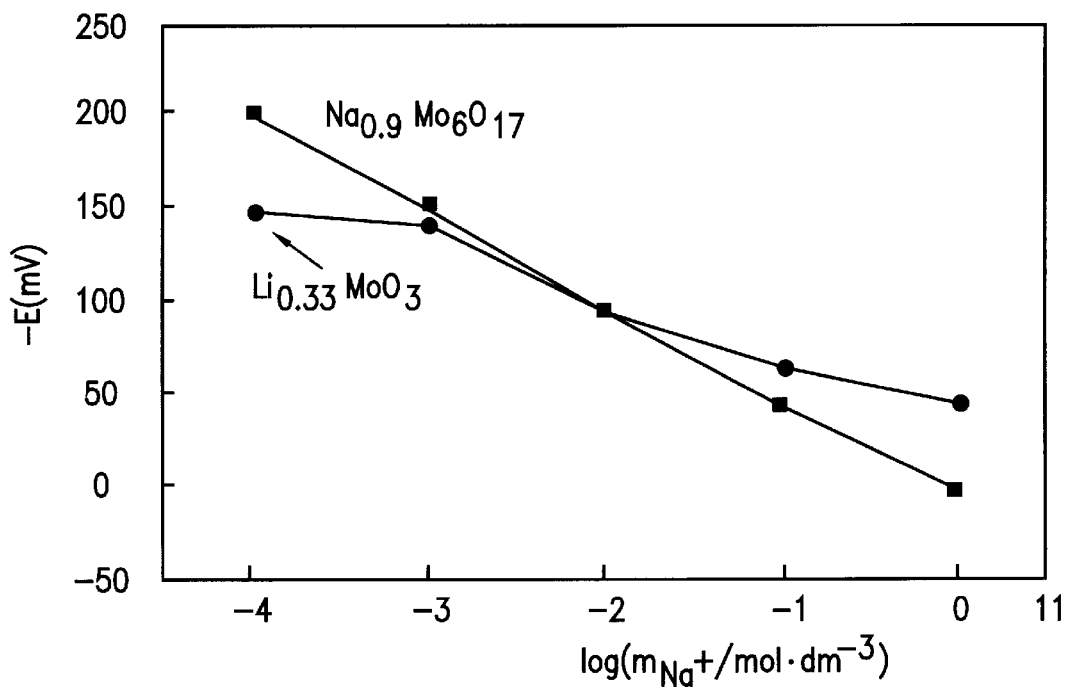
FIG. 12 is a graph showing the potentials of $A_xMo_yO_z$ electrodes of the present invention vs. Ag/AgCl reference electrode as a function of $Na^+$ concentration in NaCl solutions.
Figure 13:
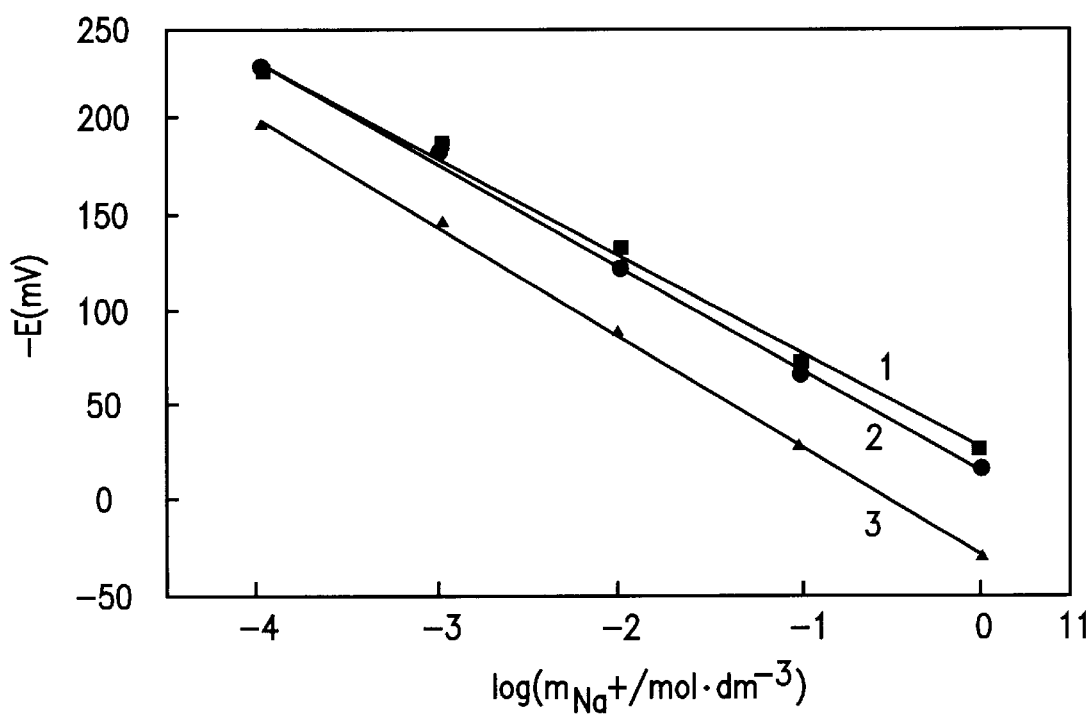
FIG. 13 is a graph showing the potentials of different $Na_{0.9}Mo_6O_{17}$ electrodes according to the present invention vs. Ag/AgCl reference electrode as a function of $NaNO_3$ concentrations.

As shown in FIG. 12, sodium ion sensors of the present invention with Li- and Na-molybdenum bronze single crystal as the sensitive electrode show quite different behavior. The sodium molybdenum bronze sensor has linear behavior between sodium ion concentrations of $10^{-4}$ and $1\ mol\cdot dmn^{-3}$ with a quasi-Nemstian slope of −52 mV/pNa, which is practically the same for different sensor samples (FIG. 13). The lithium molybdenum bronze sensor shows deviation from linearity at low and high sodium ion concentrations. Based on the response tests of several sensors of the present invention, it is reasonable to assume that the sodium ion activity in the subsurface layer of sodium molybdenum bronze is nearly constant at the conditions of the measurements.

Figure 14:
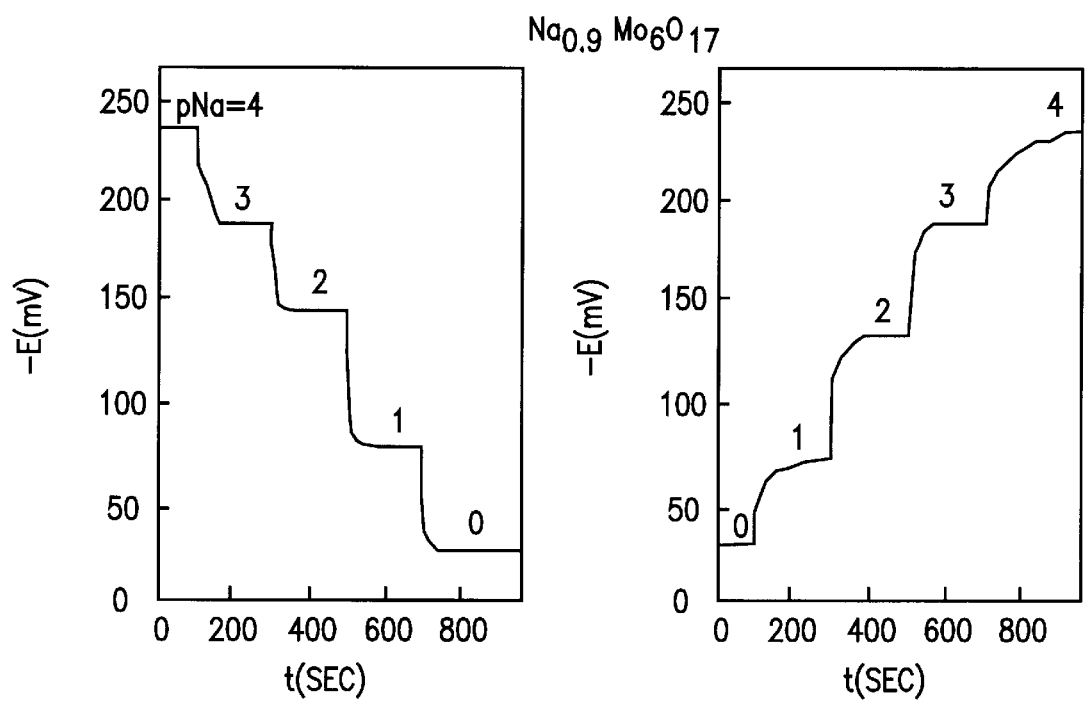
FIG. 14 is a graph showing the dynamic pNa response of $Na_{0.9}Mo_6O_{17}$ sensors according to the present invention in $NaNO_3$ solutions (pNa=$-\log a_{Na^+}$).

The sodium ion sensors of the present invention with the Na-molybdenum-oxide bronze are extremely sensitive to changes of $Na^+$ concentration of the analyte. FIG. 14 represents typical dynamic behavior of $Na_{0.9}Mo_6O_{17}$ sensors as a function of the $Na^+$ concentration in the analyte. The response time of the $Na_{0.9}Mo_6O_{17}$ sensor to changes of sodium ion concentration in a wide concentration range was less than 10 seconds for 90% response, except at low sodium ion concentration (i.e. $10^{-4}\ mol\cdot dm^{-3}$). In the latter case, sodium ion exchange was probably the limiting factor. Thus, the sodium ion sensors of the present invention show good stability in a wide range of sodium ion concentrations.

Figure 15:
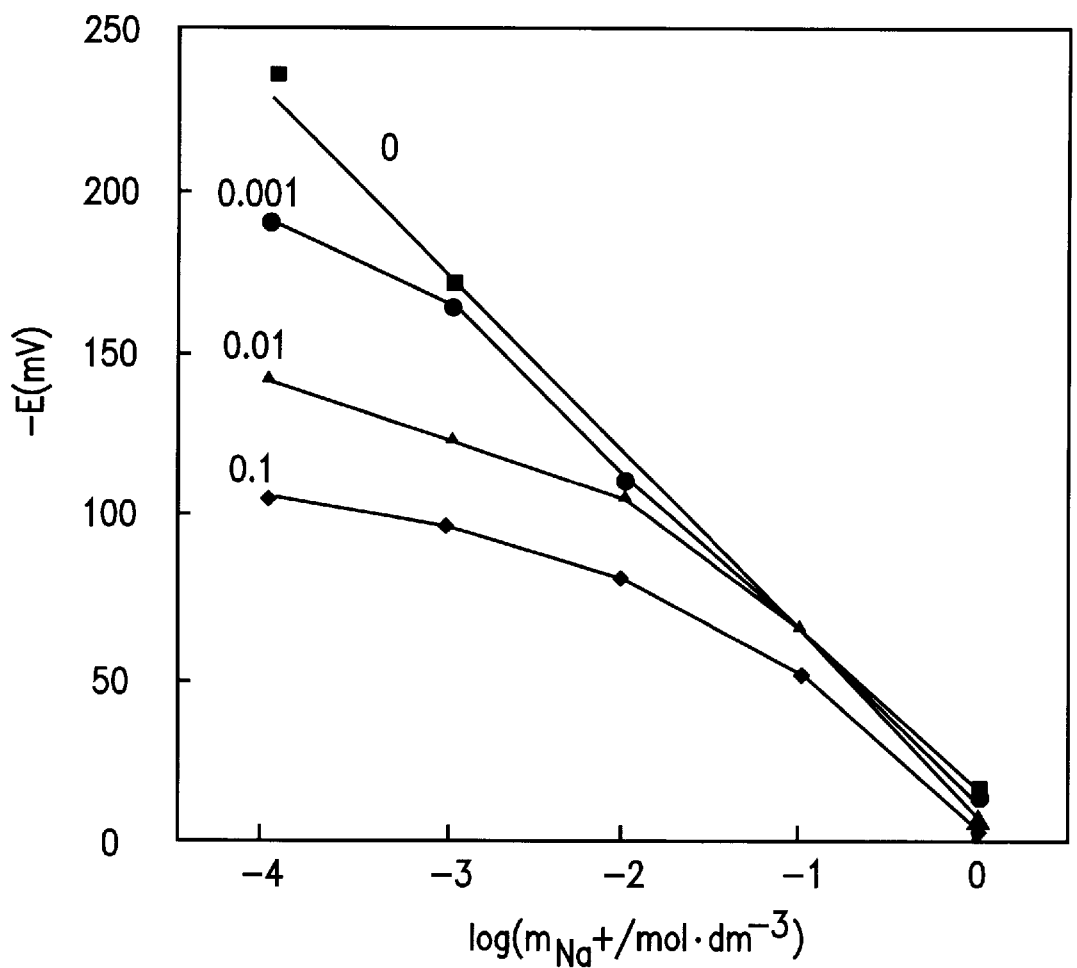
FIG. 15 is a graph showing cross sensitivity tests of a $Na_{0.9}Mo_6O_{17}$ sensor to $K^+$ ions in $NaNO_3$ solutions containing constant $K^+$ concentrations ($mol \cdot dm^{-3}$).
Figure 16:
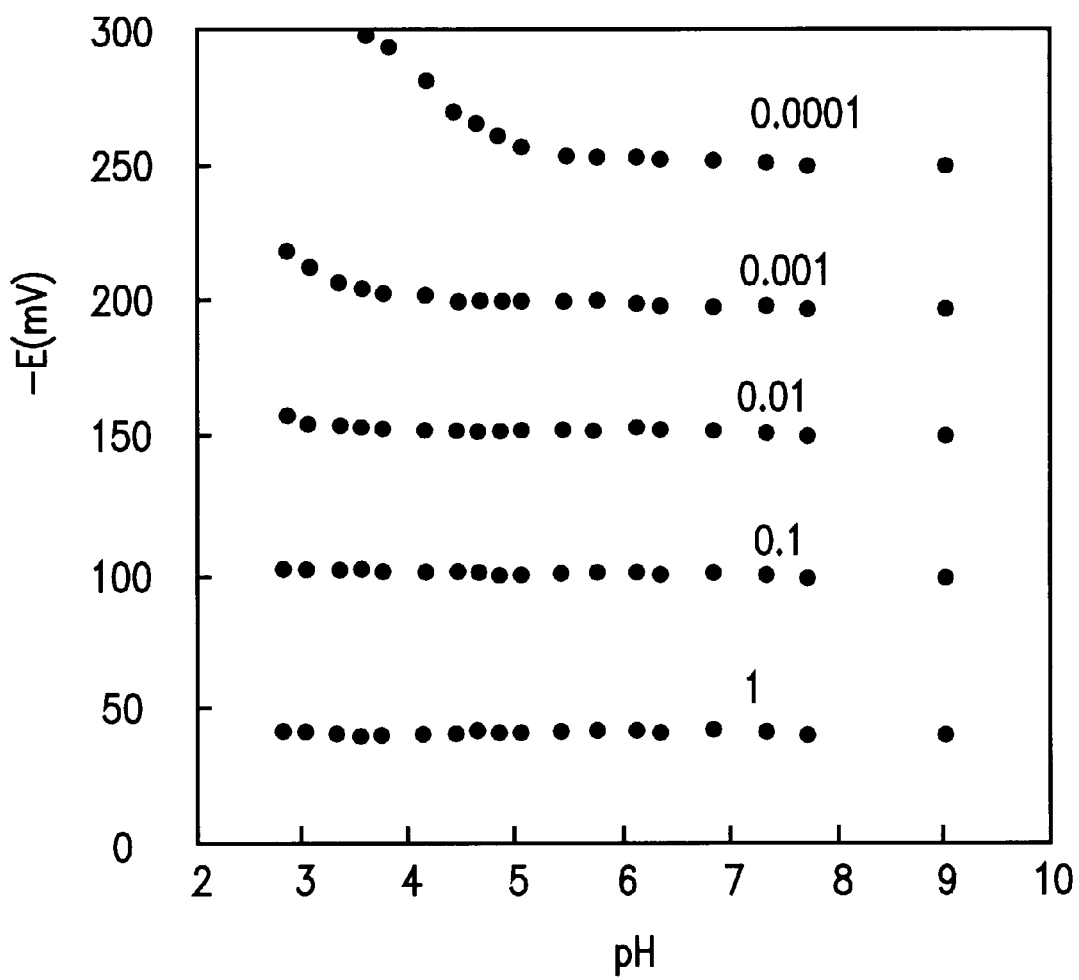
FIG. 16 is a graph showing cross sensitivity tests of a $Na_{0.9}Mo_6O_{17}$ sensor to $H^+$ ions in $NaNO_3$ solutions (marked sodium ion concentrations in $mol \cdot dm^{-3}$).
Figure 17:
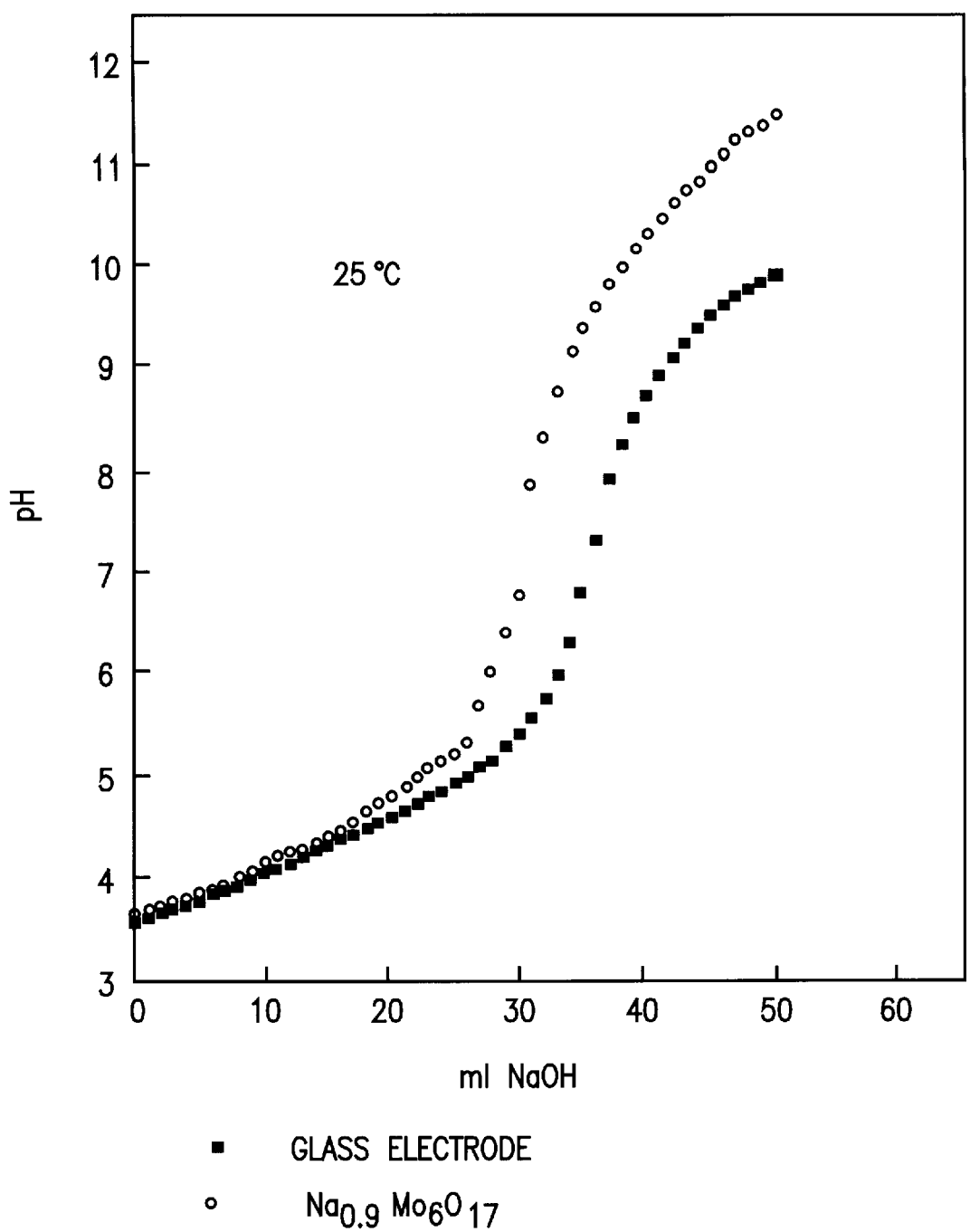
FIG. 17 is a graph showing comparing the sensitivity of a $Na_{0.9}Mo_6O_{17}$ sensor according to the present invention and a glass electrode to change in pH during the titration of apple juice with 0.1M NaOH.
Figure 18:
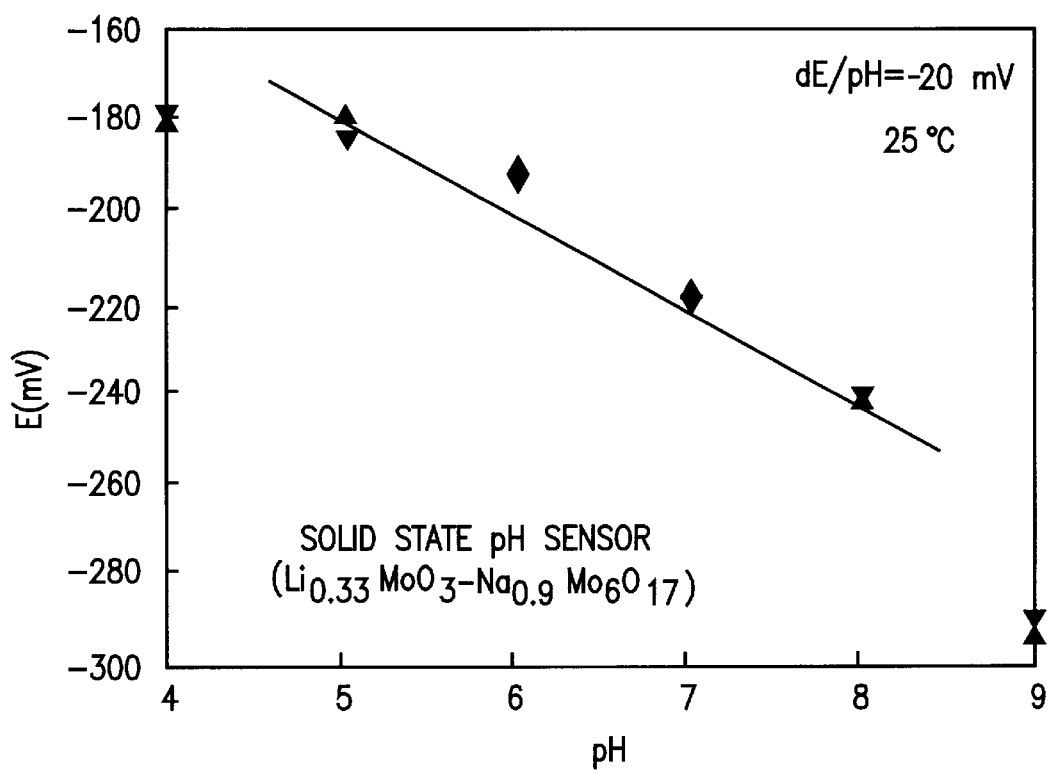
FIG. 18 is a graph showing the response of a solid state $Li_{0.33}MoO_3$-$Na_{0.9}Mo_6O_{17}$ pH sensor according to the present invention.

Cross-sensitivity tests of sodium ion sensors with single crystals of $Na_{0.9}Mo_6O_{17}$ show significant selectivity error in solutions containing $K^+$ or $H^+$ (FIGS. 15, 16). For comparison the curve (0) shown in FIG. 15 gives data of the sodium molybdenum bronze electrode behavior in a solution containing only sodium nitrate. Clearly, the molybdenum bronze electrode has an appreciable cross sensitivity to potassium ions, particularly when the potassium ion concentration is comparable or higher than that of the sodium ion. A marked response to changes in proton concentration at low pH was noted in dilute sodium nitrate solutions, i.e., <0.01 mol·dm$^{-3}$ (FIG. 16). As might be expected, the higher the sodium ion concentration, the less is the effect of pH, even at low pH values. In the pH range of 3–9, however, the solution of pH appears to have little effect on the sodium ion concentration sensing properties of the sodium molybdenum bronze electrode of the present invention when the sodium ion concentration is over 0.01 mol·dm$^{-3}$.

pH measurements in several liquid foods with a prototype molybdenum oxide bronze sensor of the present invention shows relatively good agreement with pH glass electrode measurements (Table 1). At 25° C., for example, the titration curves of apple juice with 0.1 M NaOH using a Na$_{0.9}$Mo$_6$O$_{17}$ of the present invention and glass electrodes are substantially equivalent (FIG. 17).

TABLE I pH Tests in Liquid Foods at 25° C.

| Food Product | Glass pH Electrode pH | Li$_{0.33}$MoO$_3$-Sensor pH | Li$_{0.33}$MoO$_3$-Sensor E, mV | Na$_{0.9}$Mo$_6$O$_{17}$-Sensor 1 pH | Na$_{0.9}$Mo$_6$O$_{17}$-Sensor 1 E, mV | Na$_{0.9}$Mo$_6$O$_{17}$-Sensor 2 pH | Na$_{0.9}$Mo$_6$O$_{17}$-Sensor 2 E, mV |
|---|---|---|---|---|---|---|---|
| Apple Juice | 3.69 | 3.65 | −118 | 3.74 | −145 | 3.80 | −148 |
| Milk | 6.56 | 5.84 | −249 | 6.10 | −274 | 6.19 | −279 |

In summary, single crystals of molybdenum bronze A$_x$Mo$_y$O$_z$ of the present invention can be fabricated into electrodes by direct solid state contact. The present electrodes are new metal-oxide-type pH and sodium-ion-sensitive electrodes. These sensors respond to changing pH and sodium ion concentration in the analyte rapidly and show good reproducibility in the range of pH 3–9 or sodium ion concentration of 1–10$^{-4}$ mol·dm$^{-3}$ and near Nernstian behavior. The sodium molybdenum bronze electrodes of the present invention are suitable for the determination of sodium ion content, particularly when the interfering ions (i.e., K$^+$ or H$^+$) are present in a concentration range at least an order of magnitude smaller than the sodium ion concentration to be determined.

The invention being thus described, it will be obvious that the same may be varied in many ways. Such variations are not to be regarded as a departure from the spirit and scope of the invention and all such modifications are intended to be included within the scope of the following claims.

What is claimed is:

1. An apparatus for detecting ion concentration in an analyte comprising:
   a) an elongate, generally cylindrical housing having a proximal end and a distal end, a hollow inner core and an outer surface;
   b) a stoichiometric molybdenum oxide bronze ion sensor supported at one end of said housing for contacting said analyte and detecting said ion concentration therein by establishing an electrical potential corresponding to said ion concentration in said analyte, said ion sensor undergoing ion-exchange with said analyte; and
   c) a processing means operatively connected to said sensor for converting said electrical potential into a measurement of ion concentration.

2. The apparatus of claim 1 further including a display means for displaying said measurement.

3. The apparatus of claim 1 further including a conductor for conducting electrical current between said ion sensor and said display means.

4. The apparatus of claim 3 further including a conductive adhesive connecting said ion sensor to said conductor.

5. The apparatus of claim 3, wherein said conductor is a wire made from a material selected from the group consisting of platinum, gold, copper, silver, aluminum, tungsten, nickel, iron, constantan, nichrome, calorite and combinations thereof.

6. The apparatus of claim 1 further including a coating disposed on said outer surface of said housing for isolating said housing from said analyte.

7. The apparatus of claim 6, wherein said coating is selected from the group consisting of non-conductive polymers, ceramics and composites.

8. The apparatus of claim 6, wherein said coating is an epoxy resin.

9. The apparatus of claim 1, wherein said molybdenum oxide bronze ion sensor is defined by:

$$A_xMo_yO_z \quad (I)$$

wherein A is Li, Na or K, Rb, Cs and Tl; 0<x≦1, y≦100 and z≦100.

10. The apparatus of claim 9, wherein a sensitive element of same molybdenum oxide bronze ion sensor is A$_{0.9}$Mo$_6$O$_{17}$ wherein A is Li, Na, K, (Na/Li), (Na/Rb), (Na/Cs).

11. The apparatus of claim 1, wherein said molybdenum oxide bronze ion sensor is a single crystal or a membrane.

12. The apparatus of claim 1, wherein a sensitive element of said molybdenum oxide bronze ion sensor is selected from the group consisting of blue bronzes, purple bronzes, red bronzes and combinations thereof.

13. The apparatus of claim 12, wherein said molybdenum oxide bronze ion sensor is A$_{0.33}$MoO$_3$ wherein A is Li, Na, K, Rb, Cs, Tl.

14. The apparatus of claim 12, wherein said molybdenum oxide bronze ion sensor is A$_{0.3}$MoO$_3$ wherein A is K, Rb, Tl.

15. The apparatus of claim 1, wherein said ion concentration is a hydrogen ion, sodium ion or potassium ion concentration.

16. The apparatus of claim 1, wherein said housing is a tube made from a material selected from the group consisting of ceramics, polymers, composites and combinations thereof.

17. A composition for detecting ion concentration in an analyte comprising a stoichiometric molybdenum oxide bronze undergoing ion-exchange with said analyte defined by A$_x$Mo$_y$O$_z$(I), wherein A is a group I or a group II metal, 0<x≦1, y≦100 and z≦100.

18. The composition of claim 17, wherein said molybdenum oxide bronze is selected from the group consisting of blue bronzes, purple bronzes, red bronzes and combinations thereof.

19. The composition of claim 17, wherein said molybdenum oxide bronze is selected from the group consisting of K$_{0.3}$MoO$_3$, Tl$_{0.3}$MoO$_3$, Rb$_{0.3}$MoO$_3$, Li$_{0.33}$MoO$_3$, Na$_{0.9}$Mo$_6$O$_{17}$, K$_{0.9}$Mo$_6$O$_{17}$, Tl$_{0.9}$Mo$_6$O$_{17}$, Li$_{0.9}$Mo$_6$O$_{17}$, K$_{0.33}$MoO$_3$, Tl$_{0.33}$MoO$_3$, Rb$_{0.33}$MoO$_3$, Cs$_{0.33}$MoO$_3$, (Na$_{0.5}$Li$_{0.5}$)$_{0.9}$Mo$_6$O$_{17}$ and combinations thereof.

20. The composition of claim 17, wherein said molybdenum oxide bronze is selected from the group consisting of single crystals, polycrystalline membranes, and thick or thin films.

Figure 2:
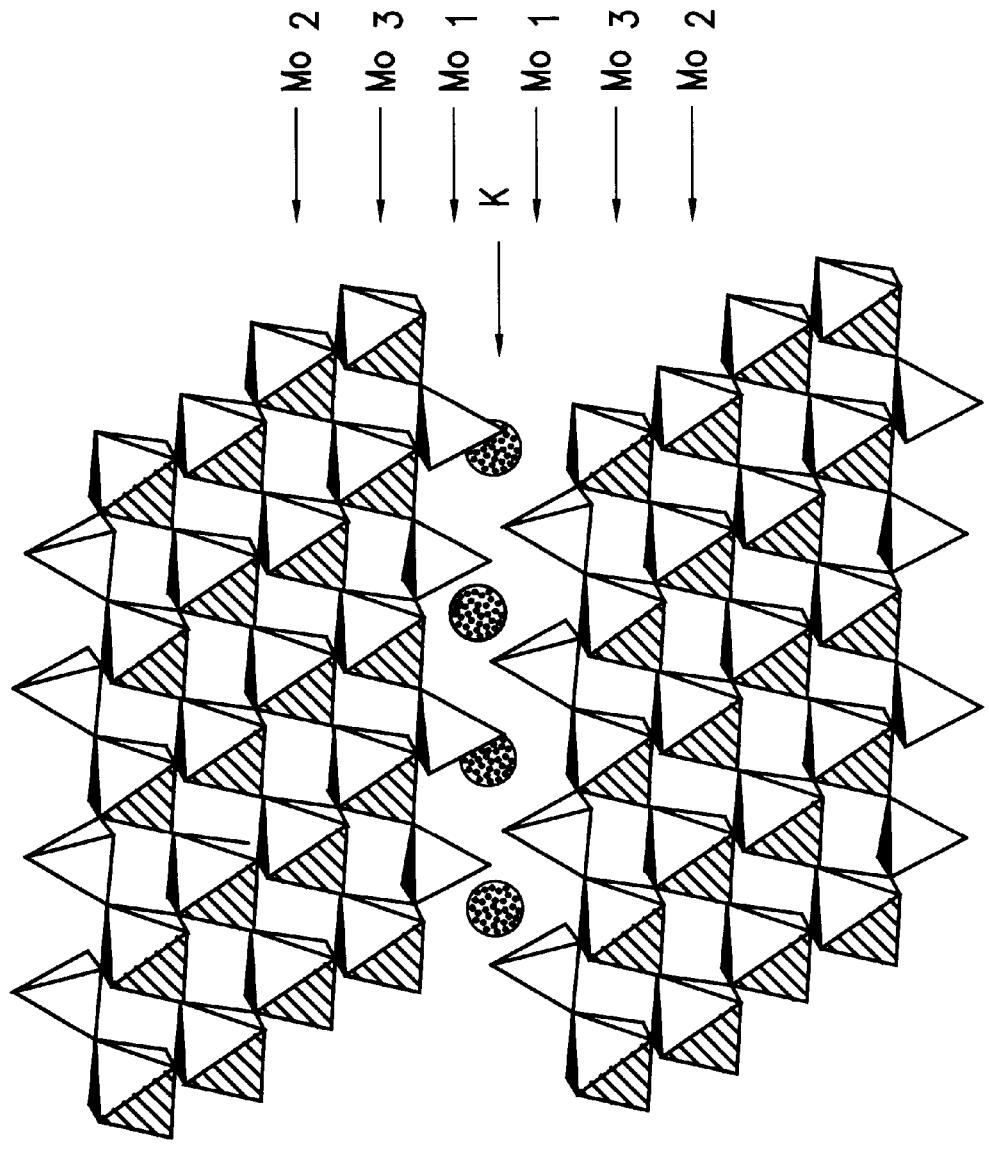
FIG. 2 is a crystal structure of $K_{0.9}Mo_6O_{17}$ according to the present invention.

21. The composition of claim 20, wherein said single crystal has a structure selected from the group consisting of K$_{0.9}$Mo$_6$O$_{17}$, K$_{0.3}$MoO$_3$ and Li$_{0.33}$MoO$_3$ as shown in FIGS. 2, 3 and respectively.

22. The composition of claim 17 adapted for use as a pH, sodium ion or potassium ion sensor for detecting pH, sodium and potassium ion concentrations in an analyte.

23. The composition of claim 17 adapted for use as a pH and sodium ion sensor for use in the food, automobile, health-related, industrial waste, and rain water industries.

24. An apparatus for detecting ion concentrations in an analyte comprising:
   a) an elongate probe having a hollow interior and an outer surface adapted to withstand variations in temperature and pH, said probe having a proximal end and a distal end;
   b) a stoichiometric metal oxide ion sensor supported at one end of said probe for contacting said analyte and detecting said ion concentration in said analyte by generating an electrical potential corresponding to ion concentration in said analyte, said ion sensor undergoing ion-exchange with said analyte; and
   c) a processing means operatively connected to said ion sensor for converting said electrical potential into a measurement of ion concentration.

25. The apparatus of claim 24, wherein said stoichiometric metal oxide ion sensor is a pH, sodium and potassium ion sensor based on a stoichiometric molybdenum oxide bronze crystal or membrane.

26. The apparatus of claim 24, wherein said temperature variation is between about 20° C. to about 200° C. and said pH variation is between about 3 to about 9.

27. A method of detecting ions in an analyte comprising the steps of:
   a) contacting an analyte with an ion detection apparatus comprising a solid state stoichiometric metal oxide ion sensor, said sensor having a crystal lattice capable of ion exchange with said analyte to form an electrical potential;
   b) measuring an electrical signal generated by said electrical potential; and
   c) converting said electrical signal into a measurement of ion concentration.

28. The method of claim 27, wherein said metal oxide ion sensor corresponds with the formula $A_xMo_yO_z$ (I), wherein A is a group I or a group II metal, $0<x\leq1$, $y\leq100$ and $z\leq100$.

* * * * *

UNITED STATES PATENT AND TRADEMARK OFFICE
CERTIFICATE OF CORRECTION

PATENT NO. : 6,015,481
DATED : January 18, 2000
INVENTOR(S) : Greenblatt, et. al.

It is certified that error appears in the above-indentified patent and that said Letters Patent is hereby corrected as shown below:

At column 3, line 5, the printed patent incorrectly reads "in a number of fermentation processes." The patent should read -- in a number of different industries. For example, pH is used to optimize the growth of microorganisms during the fermentation process. --

At column 7, line 37, the printed patent incorrectly reads "O<X≤ 51". The patent should read -- O<X ≤ 1 --.

At column 9, line 34, the printed patent incorrectly reads "ininite". The patent should read -- infinite --.

At column 9, line 54, the printed patent incorrectly reads "comer". The patent should read -- corner --.

At column 13, lines 57-58, the printed patent incorrectly reads "Y<100 and Z<100". The patent should read -- y≤100 and z≤100 --.

At column 14, line 20, the printed patent incorrectly reads "$Na_{0.9} Mo_6 O_7$". The patent should read -- $Na_{0.9} Mo_6 O_{17}$ --.

In claim 21, the printed patent incorrectly reads "2,3 and respectively." The patent should read -- 2,3 and 4, respectively . --

Signed and Sealed this

Twentieth Day of March, 2001

Attest:

NICHOLAS P. GODICI

Attesting Officer      Acting Director of the United States Patent and Trademark Office